United States Patent
Heidecke et al.

(10) Patent No.: US 10,732,184 B2
(45) Date of Patent: Aug. 4, 2020

(54) DIAGNOSIS OF CANCER BY DETECTING AUTO-ANTIBODIES AGAINST PAR1

(71) Applicant: CELLTREND GMBH, Luckenwalde (DE)

(72) Inventors: Harald Heidecke, Berlin (DE); Kai Schulze-Forster, Berlin (DE)

(73) Assignee: CellTrend GmbH, Luckenwalde (DE)

( * ) Notice: Subject to any disclaimer, the term of this patent is extended or adjusted under 35 U.S.C. 154(b) by 86 days.

(21) Appl. No.: 15/115,891

(22) PCT Filed: Feb. 3, 2015

(86) PCT No.: PCT/EP2015/052190
§ 371 (c)(1),
(2) Date: Aug. 1, 2016

(87) PCT Pub. No.: WO2015/117956
PCT Pub. Date: Aug. 13, 2015

(65) Prior Publication Data
US 2017/0168066 A1 Jun. 15, 2017

(30) Foreign Application Priority Data
Feb. 4, 2014 (EP) .................................... 14153826

(51) Int. Cl.
| | | |
|---|---|---|
| *C07K 16/22* | (2006.01) | |
| *G01N 33/68* | (2006.01) | |
| *G01N 33/574* | (2006.01) | |
| *G01N 33/564* | (2006.01) | |
| *G01N 33/74* | (2006.01) | |
| *C07K 16/28* | (2006.01) | |

(52) U.S. Cl.
CPC ......... *G01N 33/6854* (2013.01); *C07K 16/22* (2013.01); *C07K 16/2863* (2013.01); *G01N 33/564* (2013.01); *G01N 33/57449* (2013.01); *G01N 33/74* (2013.01); *C07K 2317/21* (2013.01); *C07K 2317/24* (2013.01); *G01N 2800/52* (2013.01); *G01N 2800/56* (2013.01)

(58) Field of Classification Search
CPC .............................. G01N 33/6854; C07K 16/22
USPC .......................................................... 435/7.23
See application file for complete search history.

(56) References Cited

U.S. PATENT DOCUMENTS

2006/0263835 A1   11/2006   Wallukat

FOREIGN PATENT DOCUMENTS

| EP | 1890150 A1 | 2/2008 |
|---|---|---|
| EP | 2613151 A1 | 7/2013 |
| WO | 2005043165 A2 | 5/2005 |
| WO | 2009/098689 A1 | 8/2009 |

OTHER PUBLICATIONS

Cheung, W. et al, Arterioscler Thromb Vasc Biol, 19: 3124-3024, 1999.*
Sagar et al (Curr Oncol, 2006, 13(1): 14-26).*
Baselga et al (Cancer Res, 1998, 58(13): 2825-2831).*
Gandhi et al (JBC, 2010, 285(20): 1593-1598).*
Kim et al (Clinical Cancer Research, 2003, 9: 4782-4791).*
Slamon et al (NEJM, 2001, 344(11): 783-792).*
Tai et al (Gynecol Oncol, 2006, 101(1): 184-185).*
International Search Report of PCT/EP2015/052190 dated Apr. 24, 2015.

* cited by examiner

*Primary Examiner* — Sean E Aeder
(74) *Attorney, Agent, or Firm* — McBee Moore & Vanik, IP, LLC

(57) ABSTRACT

The present invention relates to a method for diagnosis of a cancer, comprising the steps of (i) determining the level of antibodies against protease-activated receptor 1 (PAR1) in a sample from a subject to be diagnosed, (ii) comparing the determined level in the sample to a control level derived from subjects without ovarian cancer; wherein a decreased level in the sample from the subject to be diagnosed as compared to the control level is indicative for ovarian cancer in the subject. Furthermore the invention relates to differential diagnosis of cancer and the prediction of the response of a subject to be treated for cancer with a drug.

25 Claims, 15 Drawing Sheets
Specification includes a Sequence Listing.

A

B

C

D

DIAGNOSIS OF CANCER BY DETECTING AUTO-ANTIBODIES AGAINST PAR1

CROSS-REFERENCE TO RELATED APPLICATIONS

This application is a National Stage entry of International Application No. PCT/EP2015/052190, filed Feb. 3, 2015, which claims priority to European Patent Application No. 14153826.4, filed Feb. 4, 2014.

FIELD OF THE INVENTION

The present invention is in the field of diagnostics, prognosis and therapeutics for cancer, more in particular in the field of diagnosis and therapy of ovarian cancer, a solid organ cancer, squamous cell carcinoma, squamous cell carcinoma, metastatic cancer, and epithelial cancer, more particular in the field of diagnosis, prognosis and therapy of ovarian cancer.

BACKGROUND OF THE INVENTION

According to the American Cancer Society ovarian cancer is expected to account for over 22,000 new cancer diagnoses and more than 14,000 deaths in 2013 in the US alone. Of the gynaecologic malignancies, ovarian cancer has the highest mortality rate. In early stages of the disease, ovarian cancer is nearly asymptomatic. Hence, a large portion of the patients present with clinically advanced stages of ovarian cancer. However, the 5-year survival rate for patients diagnosed with early-stage disease is often >90%, but it is <20% for advanced-stage disease, underscoring the importance of early detection.

Current diagnosis of ovarian cancer relies on pelvic exam, transvaginal ultrasonography, (TVS), abdominal ultrasonography, and exploratory or diagnostic laparoscopy. The most commonly used biomarker for clinical screening and prognosis in patients with ovarian cancer is ovarian cancer antigen 125 (CA125) (Coticchia et al. (2008), J. Natl. Compr. Canc. Netw. 6(8):795-802). Serum CA125 levels are elevated in ≈80% of patients with advanced-stage epithelial ovarian cancer but are increased in only 50-60% of patients with early-stage disease. Serum CA125 levels may be falsely elevated in women with any i.p. pathology resulting in irritation of the serosa of the peritoneum or pericardium, uterine fibroids, renal disorders, and normal menses. Moreover, serum CA125 levels do not predict the outcome of cytoreductive surgery in patients with advanced epithelial ovarian cancer. Further biomarkers include, for example, Human Epidymis Protein 4 (HE4) and Mesothelin (Sarojini et al. (2012), Journal of Oncology 102, Article ID 709049). Severeness of ovarian cancer is categorized by the grade and stage of tumorization. This nowadays can only be performed by evaluation of the tumors under or after surgical treatment or by combining marker evaluation and (histological) evaluation of tissue. Staging is very important because ovarian cancers have different prognosis at different stages and may be treated differently. The accuracy of the staging may determine whether or not a patient will be cured. If the cancer isn't accurately staged, then cancer that has spread outside the ovary might be missed and not treated. Once a stage has been given it does not change, even when the cancer comes back or spreads to new locations in the body.

Ovarian cancer staging is by FIGO staging system uses information obtained after surgery, which can include a total abdominal hysterectomy, removal of (usually) both ovaries and fallopian tubes, (usually) the omentum, and pelvic (peritoneal) washings for cytopathology. The AJCC stage is the same as the FIGO stage. The AJCC staging system describes the extent of the primary tumor (T), the absence or presence of metastasis to nearby lymph Nodes (N), and the absence or presence of distant Metastasis (M).

Stage I Limited to One or Both Ovaries
  IA involves one ovary; capsule intact; no tumor on ovarian surface; no malignant cells in ascites or peritoneal washings
  IB involves both ovaries; capsule intact; no tumor on ovarian surface; negative washings
  IC tumor limited to ovaries with any of the following: capsule ruptured, tumor on ovarian surface, positive washings
Stage II Pelvic Extension or Implants
  IIA extension or implants onto uterus or fallopian tube; negative washings
  IIB extension or implants onto other pelvic structures; negative washings
  IIC pelvic extension or implants with positive peritoneal washings
Stage III peritoneal implants outside of the pelvis; or limited to the pelvis with extension to the small bowel or omentum
  IIIA microscopic peritoneal metastases beyond pelvis
  IIIB macroscopic peritoneal metastases beyond pelvis less than 2 cm in size
  IIIC peritoneal metastases beyond pelvis >2 cm or lymph node metastases
Stage IV Distant Metastases to the Liver or Outside the Peritoneal Cavity Para-aortic lymph node metastases are considered regional lymph nodes (Stage IIIC). As there is only one para-aortic lymph node intervening before the thoracic duct on the right side of the body, the ovarian cancer can rapidly spread to distant sites such as the lung.

The AJCC/TNM staging system includes three categories for ovarian cancer, T, N and M. The T category contains three other subcategories, T1, T2 and T3, each of them being classified according to the place where the tumor has developed (in one or both ovaries, inside or outside the ovary). The T1 category of ovarian cancer describes ovarian tumors that are confined to the ovaries, and which may affect one or both of them. The sub-subcategory T1a is used to stage cancer that is found in only one ovary, which has left the capsule intact and which cannot be found in the fluid taken from the pelvis. Cancer that has not affected the capsule, is confined to the inside of the ovaries and cannot be found in the fluid taken from the pelvis but has affected both ovaries is staged as T1b. T1c category describes a type of tumor that can affect one or both ovaries, and which has grown through the capsule of an ovary or it is present in the fluid taken from the pelvis. T2 is a more advanced stage of cancer. In this case, the tumor has grown in one or both ovaries and is spread to the uterus, fallopian tubes or other pelvic tissues. Stage T2a is used to describe a cancerous tumor that has spread to the uterus or the fallopian tubes (or both) but which is not present in the fluid taken from the pelvis. Stages T2b and T2c indicate cancer that metastasized to other pelvic tissues than the uterus and fallopian tubes and which cannot be seen in the fluid taken from the pelvis, respectively tumors that spread to any of the pelvic tissues (including uterus and fallopian tubes) but which can also be found in the fluid taken from the pelvis. T3 is the stage used to describe cancer that has spread to the peritoneum. This stage provides information on the size of the metastatic tumors (tumors that are located in other areas of the body, but are caused by ovarian cancer). These tumors can be very small, visible only under the microscope (T3a), visible but not larger than 2 centimeters (T3b) and bigger than 2 centimeters (T3c). This staging system also uses N categories to describe cancers that have or not spread to nearby lymph nodes. There are only two N categories, N0 which indicates that the cancerous tumors have not affected the lymph nodes, and N1 which indicates the involvement of lymph nodes close to the tumor. The M categories in the AJCC/TNM staging system provide information on whether the ovarian cancer has metastasized to distant organs such as liver or lungs. M0 indicates that the cancer did not spread to distant organs and M1 category is used for cancer that has spread to other organs of the body.

The AJCC/TNM staging system also contains a Tx and a Nx sub-category which indicates that the extent of the tumor cannot be described because of insufficient data, respectively the involvement of the lymph nodes cannot be described because of the same reason. The ovarian cancer stages are made up by combining the TNM categories in the following manner:

Stage I: T1+N0+M0; IA: T1a+N0+M0; IB: T1b+N0+M0; IC: T1c+N0+M0;

Stage II: T2+N0+M0; IIa: T2a+N0+M0; IIB: T2b+N0+M0; IIC: T2c+N0+M0;

Stage III: T3+N0+M0; IIIA: T3a+N0+M0; IIIB: T3b+N0+M0; IIIC: T3c+N0+M0 or any T+N1+M0;

Stage IV: Any T+ Any N+M1

In addition to being staged, like all cancers ovarian cancer is also graded. The histologic grade of a tumor measures how abnormal or malignant its cells look under the microscope. There are four grades indicating the likelihood of the cancer to spread and the higher the grade, the more likely for this to occur. Grade 0 is used to describe non-invasive tumors. Grade 0 cancers are also referred to as borderline tumors. Grade 1 tumors have cells that are well differentiated (look very similar to the normal tissue) and are the ones with the best prognosis. Grade 2 tumors are also called moderately well differentiated and they are made up by cells that resemble the normal tissue. Grade 3 tumors have the worst prognosis and their cells are abnormal, referred to as poorly differentiated.

Cancer staging can be divided into a clinical stage and a pathologic stage. In the TNM (Tumor, Node, Metastasis) system, clinical stage and pathologic stage are denoted by a small "c" or "p" before the stage (e.g., cT3N1M0 or pT2N0). Clinical stage is based on all of the available information obtained before a surgery to remove the tumor. Thus, it may include information about the tumor obtained by physical examination, radiologic examination, and endoscopy. Pathologic stage adds additional information gained by examination of the tumor microscopically by a pathologist.

Because they use different criteria, clinical stage and pathologic stage often differ. Pathologic staging is usually considered the "better" or "truer" stage because it allows direct examination of the tumor and its spread, contrasted with clinical staging which is limited by the fact that the information is obtained by making indirect observations of a tumor which is still in the body. However, clinical staging and pathologic staging still has to be complemented by each other. Not every tumor is treated surgically, therefore pathologic staging is not always available. Also, sometimes surgery is preceded by other treatments such as chemotherapy and radiation therapy which shrink the tumor, so the pathologic stage may underestimate the true stage.

In the minority of cases (5-10 percent) cancers are caused by an altered gene that is inherited. The abnormal growth, invasive properties and treatment resistance of the other 90-95 percent of cases are caused by acquired mutated genes or misregulated genes; i.e. they are not inherited and hence are unique to the developing tumor. Such abnormalities may affect many aspects of cell behaviour including the control of expression of other genes (epigenetic regulators). In addition risk factors can be present which are thought to be associated with the acquiring of cancer. Risk factors can be subdivided into those that can be altered and those that cannot. Examples of lifestyle factors that appear to affect the risk of cancer include smoking, exercise, weight, and alcohol use. Examples of risk factors that are not modifiable include age, gender, and family history. While there is sometimes a correlation between the type of cancer and exposure to certain toxins (such as lung cancer and smoking), most of the time the cause of cancer remains a mystery.

Although cancer often appears suddenly, most cancers grow slowly and remain without symptoms for several years. Hence, they may be advanced before they got detected. A cancer that has acquired aggressive properties, however, can seem to appear out of nowhere and cause death within months. Unfortunately, very little is known about the biologies that explain these different behaviours and outcomes.

If solid tumours are benign (harmless) and stay in their place of origin, they can generally be removed and pose no long-term threat. However, solid tumours that have acquired aggressive properties are able to spread (metastasize) via the blood or lymphatic (immune) systems to another part of the body. Once cancers metastasize the prognosis for the patient becomes poor, but why some tumours metastasize and others do not is still a mystery.

Staging is an important part of cancer diagnosis because it can be used to guide therapeutic decisions based on historical experience of particular outcomes after different treatments. In the TNM system of staging, the combination of the tumour size (T), the number of lymph nodes involved (N) and whether metastases are detectable (M) provides details which place the overall stage of the cancer at 0, I, II, III or IV. Some cancers also have particular cell surface receptors that give them a growth advantage, and knowing the receptor status can provide an even more in-depth assessment of the cancer's stage. In addition to staging factors, the likely outcome (or prognosis), may also be affected by the age, and health status of an individual. This staging system is used for most forms of cancer, except brain tumors and hematological malignancies. For solid tumors, TNM is by far the most commonly used system, but it has been adapted for some conditions.

However, there is a need for improved tools for the diagnosis, early detection; staging, grading and prognosis of cancer, e.g. a solid organ cancer, like ovarian cancer, squamous cell cancer, and metastatic cancer. In particular there is a need for predicting response to a cancer treatment.

The inventors found that the level of autoimmuneantibodies is a well suited predictor for the diagnosis, early detection, staging, and grading of tumors, Furthermore, it is possible to predict whether a patient to be treated or being treated for cancer will respond to said treatment. The invention hence solves the outlined problems and overcomes the drawbacks of the state of the art.

SUMMARY OF THE INVENTION

Subject of the invention is a method for diagnosis of a cancer, comprising the steps of
  (i) determining the level of antibodies against protease-activated receptor 1 (PAR1) in a sample from a subject to be diagnosed,
  (ii) comparing the determined level in the sample to a control level derived from subjects without cancer;
wherein a decreased level in the sample from the subject to be diagnosed as compared to the control level is indicative for cancer in the subject.

The invention further pertains to a method for diagnosis of a cancer, wherein the level of antibodies against protease-activated receptor 1 (PAR1) is determined in a sample from a subject to be diagnosed and wherein a level of anti-PAR1 antibodies below 4 units/ml is indicative for cancer, preferably a level of anti-PAR1 antibodies below 3.5 units/ml, more preferably below 3 units/ml, more preferably below 2.7 units/ml, also preferred below 2.5 units/ml is indicative for cancer.

The present invention is further directed to an immunoassay method for detecting an anti-PAR1 antibody in a sample from a subject, comprising the steps of
  (a) contacting the sample suspected of comprising an anti-PAR1 antibody with protease-activated receptor 1 (PAR1) or an antigenic peptide fragment thereof under conditions allowing for the formation of a complex between the anti-PAR1 antibody with PAR1 or the peptide fragment thereof,
  (b) detecting the complex.

In the context of the present invention PAR1 or an antigenic peptide fragment thereof can thus be used for the diagnosis of cancer.

The present invention further relates to research and/or diagnostic kit for the diagnosis of cancer, wherein the kit comprises PAR1 or an antigenic peptide fragment thereof.

The inventors also found that the level of antibodies against PAR1 correlates with the risk of relapse or mortality in subjects treated with an angiogenesis inhibitor or an inhibitor of EGFR activity. Decreased levels of anti-PAR1 antibodies in samples correlated with a higher risk of relapse or mortality in patients treated with an angiogenesis inhibitor or an inhibitor of EGFR activity. Hence, levels of anti-PAR1 antibodies in samples of patients to be treated with an angiogenesis inhibitor or an inhibitor of EGFR activity are an indicator for response or non-response of a patient, i.e. whether improvement of the disease is achieved in a patient (responder) or not (non-responder). If a patient responds to a treatment the disease is ameliorated. It might be the case that a patient responds to a treatment at first but suffers from relapse of the disease at a later stage. Also this is a form of non-response. Therefore, the invention also relates to a method for determining whether a subject being treated or to be treated for cancer with a drug will respond to said treatment comprising the steps of
  (i) determining the level of antibodies against protease-activated receptor 1 (PAR1) in a sample from said subject being treated or to be treated; and
  (ii) comparing the determined level in the sample to either one or both of a first and second PAR1 antibody control level,
    a) wherein the first PAR1 antibody control level is derived from subjects responding to said treatment, and
    b) wherein the second PAR1 antibody control level is derived from subjects not responding to said treatment,
wherein a decreased level in the sample from the subject being treated or to be treated as compared to the first PAR1 antibody control level and/or an equal level as compared to the second PAR1 antibody control level is indicative for a non-response of said subject to said treatment, and wherein an increased level in the sample from the subject being treated or to be treated as compared to the second PAR1 antibody control level and/or an equal level as compared to the first PAR1 antibody control level is indicative for a response of said subject to said treatment. In a preferred embodiment of the invention the subject is to be treated, i.e. the method to determine response of a subject is performed before the onset of treatment. In a preferred embodiment the drug is an angiogenesis inhibitor according to the present invention.

The present invention also relates to a method of treating cancer in a subject, comprising determining the level of antibodies against protease-activated receptor 1 (PAR1) in a sample from the subject, wherein when the level of anti-PAR1 antibodies in a sample from the subject is above the threshold determined by the method for determining response according to the present invention a drug is administered to the subject. In a preferred embodiment the drug is an angiogenesis inhibitor or an inhibitor of EGFR activity according to the present invention is administered at anti-PAR1 levels above the threshold.

The present invention also relates to a method of treating cancer in a subject with an angiogenesis inhibitor, comprising determining the level of antibodies against protease-activated receptor 1 (PAR1) in a sample from the subject, wherein when the level of anti-PAR1 antibodies in a sample from the subject is above 0.6 units/ml said angiogenesis inhibitor is administered to the subject, preferably when the level of anti-PAR1 antibodies in a sample is above 0.7 units/ml, preferably above 0.8 units/ml, more preferably above 0.9 units/ml. The angiogenesis inhibitor is preferably bevacizumab.

Furthermore, the invention relates to a method of treating cancer in a subject with an inhibitor of EGFR activity, comprising determining the level of antibodies against protease-activated receptor 1 (PAR1) in a sample from the subject, wherein when the level of anti-PAR1 antibodies in a sample from the subject is above 1.5 units/ml said inhibitor of EGFR activity is administered to the subject, preferably when the level of anti-PAR1 antibodies in a sample is above 1.7 units/ml, preferably above 2.0 units/ml, more preferably above 2.5 units/ml. The angiogenesis inhibitor is preferably panitumumab.

As outlined, results of non-response of a patient to a treatment may be relapse of ovarian cancer, death (mortality) or progression of the cancer. Hence, in a preferred embodiment of the method to determine/predict the response of a subject to a treatment the present invention also relates to a method for the prediction of risk stratification for relapse of ovarian cancer and/or mortality and/or progression of cancer in a subject being treated or to be treated for cancer with a drug, the method comprising the steps of (i) determining the level of antibodies against protease-activated receptor 1 (PAR1) in a sample from said subject to be treated or being treated with an angiogenesis inhibitor (ii) comparing the determined level in the sample to either one or both of a first and a second PAR1 antibody control level, a) wherein the first PAR1 antibody control level is derived from subjects not showing relapse or progression of cancer or mortality or after treatment with said drug, and b) wherein the second PAR1 antibody control level is derived from subjects showing relapse or progression of cancer or mortality after treatment with said drug, wherein a decreased level in the sample from the subject being treated as compared to the control level is indicative for relapse or progression of cancer or mortality in the subject. Preferably the level in said patient is determined before the onset of treatment. In a preferred embodiment of the present invention first PAR1 antibody control level is derived from subjects that did not show relapse or progression of cancer or mortality within 20 months after onset of treatment with said drug and the second PAR1 antibody control level is derived from subjects that did show relapse or progression of cancer or mortality within 20 months after onset of treatment with said drug.

As will be readily understood by the skilled person, this method may be performed as a method for monitoring treatment efficiency. In this embodiment the levels of anti-PAR1 antibodies in said subject is determined during treatment, i.e. in a subject being treated with said drug.

DETAILED DESCRIPTION OF THE INVENTION

Figure 1:
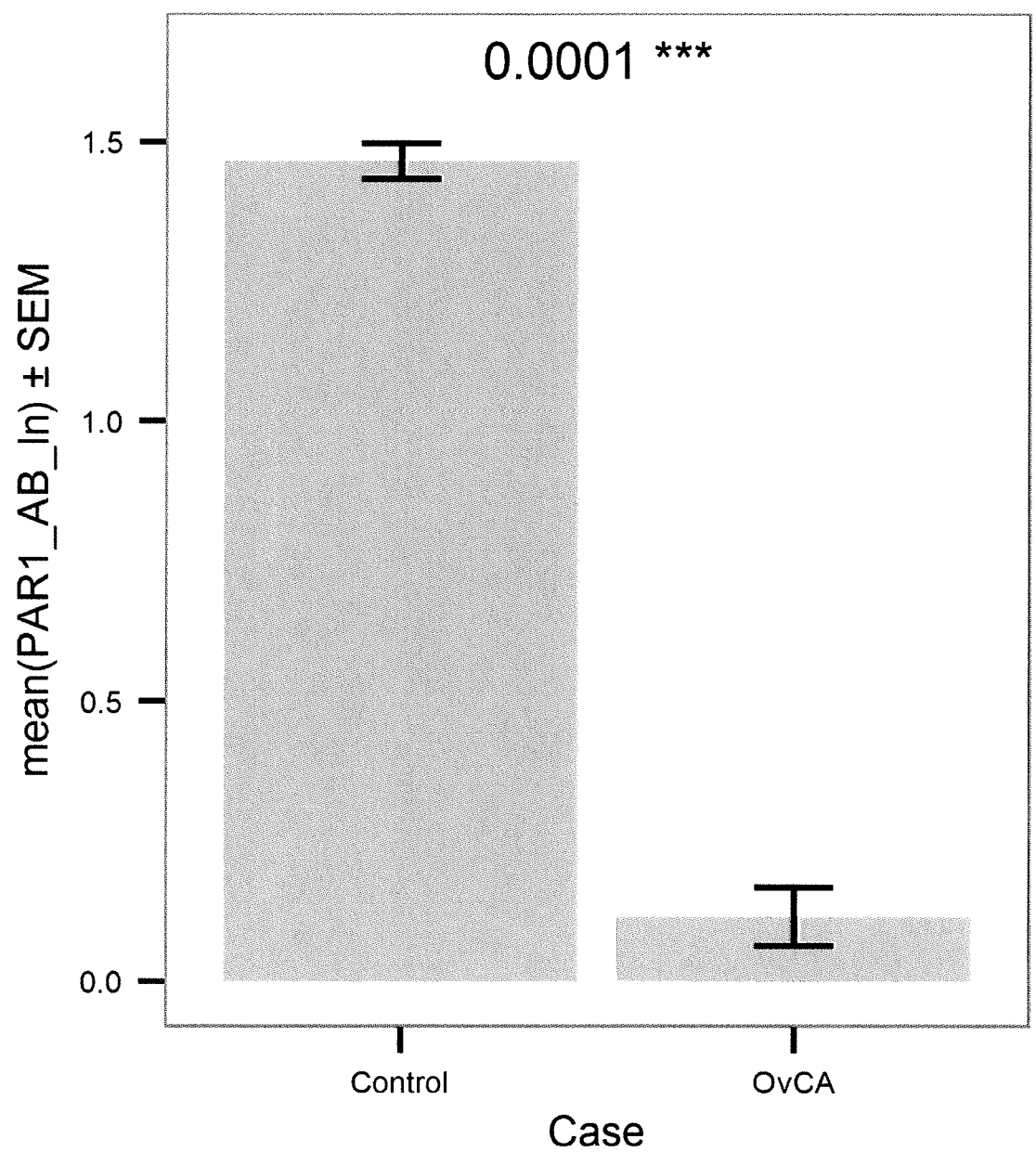
FIG. 1: Comparison of the mean level of anti-PAR1 antibodies (ln of units/ml) in serum samples of ovarian cancer patients ("OvCA"; mean ln of units/ml=0.115; n=201) to the median level of anti-PAR1 antibodies in serum samples of a healthy control group (Control, mean ln of units/ml=1.466 units/ml; n=132). The p-value is indicated on top. Bars indicate standard error of mean.

The present invention is based on the surprising finding of the inventors that in samples of patients with ovarian cancer decreased levels of anti-PAR1 antibodies can be found as compared to subjects without ovarian cancer, solid organ cancer, squamous cell carcinoma or metastatic cancer. In other words the inventors have found that patients with these cancers have little or no detectable antibodies against protease-activated receptor 1 (PAR1) in the blood, (e.g. determined in the serum or plasma) whereas in control groups anti-PAR1 auto-antibodies can be detected at higher levels.

The present invention is based on the finding of that levels of autoimmune-antibodies in subjects have diagnostic and predictive properties. The antibodies to be detected in connection with the present invention are therefore autoantibodies, i.e. those produced by immune system of the subject to be diagnosed or being or to be treated.

The inventors of the present application for the first time demonstrate the decrease of levels of anti-PAR1 antibodies in samples of subjects has a diagnostic and predictive value. It was found that a decrease in the level of antibodies directed against PAR1 in samples of a subject to be diagnosed as compared samples from subjects with proven absence of cancer is indicative for the presence of cancer as well as for the prediction of response or non-response to a treatment of the cancer with a drug. Hence, "cancer" in connection with the present invention is to be understood as any diseases involving unregulated cell growth. Cancer in this regard is a disease where cells divide and grow uncontrollably resulting in the formation of tumors, preferably malignant tumors.

Cancer refers to a mass of cells that grows in an abnormal, unregulated way and that ultimately overwhelms a body system or organ. The word 'cancer' interchangeably used herein with 'tumor'. A 'tumor' refers to any abnormal growth of cells and can be harmless or dangerous. A harmless tumor is called benign and does not contain malignant cancerous cells whereas a dangerous tumor is called malignant (meaning inherently 'bad') because it contains malignant cancerous cells.

Tumors or cancers are called 'solid' or 'liquid' based on where in the body they grow. More than 80 percent of all cancers are caused by solid tumors (solid organ cancers) that grow as a mass of cells in particular organ, tissue or gland. Common sites for solid organ cancers are ovars, breast, lung, prostate, and colon, and examples of other sites are brain, uterus, pancreas, skin, and liver. In contrast, liquid tumors, such as leukemia, develop in the blood and can travel to any part of the body (some of these are covered in the Blood Disorders section). Solid tumors are further divided into carcinomas, sarcomas or lymphomas, according to the cell types that are involved. For example, tumors that develop in skin cells or cells lining or covering the internal organs are called carcinomas whereas sarcomas develop in bone, cartilage, fat, muscle, blood vessels or connective tissue. Tumors of the lymphatic system that develop in mature immune system cells are called lymphomas. Brain tumors generally do not fall into these categories, as they may arise from cell types exclusively found in the brain.

However, in a preferred embodiment of the present invention "cancer" refers to an EGFR or EGF associated cancer. EGFR or EGF associated cancers are known by the skilled person. Mutations that lead to EGFR overexpression (known as upregulation) or overactivity have been associated with a number of cancers, including lung cancer, anal cancers (Walker F, Abramowitz L, Benabderrahmane D, Duval X, Descatoire V, Hénin D, Lehy T, Aparicio T (November 2009). "Growth factor receptor expression in anal squamous lesions: modifications associated with oncogenic human papillomavirus and human immunodeficiency virus". Hum. Pathol. 40 (11): 1517-27), ovarian cancer and glioblastoma multiforme. Mutations involving EGFR could lead to its constant activation, which could result in uncontrolled cell division—a predisposition for cancer (Lynch T J, Bell D W, Sordella R, Gurubhagavatula S, Okimoto R A, Brannigan B W, Harris P L, Haserlat S M, Supko J G, Haluska F G, Louis D N, Christiani D C, Settleman J, Haber D A (May 2004). "Activating mutations in the epidermal growth factor receptor underlying responsiveness of non-small-cell lung cancer to gefitinib". N. Engl. J. Med. 350 (21): 2129-39). Mutations, amplifications or misregulations of EGFR or family members are implicated in about 30% of all epithelial cancers. Hence, in a preferred embodiment of the present invention the cancer is an EGFR or EGF associated cancer, preferably selected from the group consisting of ovarian cancer, a solid organ cancer, squamous cell carcinoma, squamous cell carcinoma, metastatic cancer, breast cancer, lung cancer, colorectal cancer, colon cancer, renal cancer, pancreatic cancer, prostate cancer, gastric cancer, liver cancer, and a glioblastoma. In a particularly preferred embodiment the cancer according to the present invention, including all embodiments, is selected from the group consisting of ovarian cancer, a solid organ cancer, squamous cell carcinoma, squamous cell carcinoma, metastatic cancer, even more preferred the cancer is an ovarian cancer.

Ovarian cancer often derives from the epithelium of the ovary, but may also be derived from fallopian tube. However, it was found that in both cases the method of the present invention is predictive for the presence of cancer or the response to a certain treatment. Hence, in one embodiment of the present invention cancer is an ovarian cancer, the ovarian cancer being epithelial ovarian cancer or cancer derived from the fallopian tube.

Squamous-cell carcinoma or squamous cell cancer (SCC or SqCC) is a cancer of a kind of epithelial cell, the squamous cell. These cells are the main part of the epidermis of the skin, and this cancer is one of the major forms of skin cancer. However, squamous cells also occur in the lining of the digestive tract, lungs, and other areas of the body, and SCC occurs as a form of cancer in diverse tissues, including the lips, mouth, esophagus, urinary bladder, prostate, lung, vagina, and cervix, among others. SCC is a histologically distinct form of cancer. It arises from the uncontrolled multiplication of cells of epithelium, or cells showing particular cytological or tissue architectural characteristics of squamous cell differentiation, such as the presence of keratin, tonofilament bundles, or desmosomes, structures involved in cell-to-cell adhesion. SCC is still sometimes referred to as "epidermoid carcinoma" and "squamous cell epithelioma", though the use of these terms has decreased. SCC typically initially occurs in the sixth decade of life (the 50s), but is most common in the eighth decade (the 70s). It is twice as prevalent in men as in women. People with darker skin are less at risk to develop SCC. Populations with fair skin, light hair, and blue/green/grey eyes are at highest risk of developing the disease. Frequent exposure to direct, strong sunlight without adequate topical protection also increases risk. SCC as referred to herein refers to a squamous cell carcinoma in general, preferably selected from the group of squamous cell carcinoma of the skin, the digestive tract, the lung, the lips, the mouth, the esophagus, the urinary bladder, the prostate, the lung, the vagina, and the cervix, more preferably it refers to squamous cell carcinoma of the skin.

The invention in one embodiment relates to a method for the diagnosis of a cancer, comprising the steps of
(i) determining the level of antibodies against PAR1 in a sample from a subject to be diagnosed,
(ii) comparing the determined level in the sample to a control level derived from subjects without cancer;
wherein a decreased level in the sample from the subject to be diagnosed as compared to the control level is indicative for cancer in the subject. The cancer according to the invention is preferably selected from the group consisting of ovarian cancer, a solid organ cancer, squamous cell carcinoma, squamous cell carcinoma, metastatic cancer, preferably an epithelial cancer, preferably selected from the group consisting of ovarian cancer, breast cancer, renal cancer, colon cancer, colorectal cancer, and lung cancer, particularly preferred ovarian cancer.

The skilled person knows that depending on the subject, different cancers may be diagnosed. He is aware that he also may have to consider further parameters to diagnose the subject, e.g. when diagnosing ovarian cancer, the subject has to be female. In the context of the present invention the subject to be diagnosed is a mammal, preferably a human. In the context of the present invention the subject to be diagnosed is mammal, preferably a female mammal, preferably a female human subject suspected of having ovarian cancer or a female mammal, preferably a female human subject to be screened for the presence of ovarian cancer, preferably a female human subject to be treated or being treated for ovarian cancer with a drug. In a further preferred embodiment, in particular for those cancers occurring in male and female, the subject is a human, preferably a human suspected of having a cancer according to the present invention.

The invention particularly relates to a method for diagnosis of a cancer, preferably the diagnosis of ovarian cancer, wherein the level of antibodies against PAR1 is determined in a sample from a subject to be diagnosed and wherein a level of anti-PAR1 antibodies below 4 units/ml is indicative for cancer, preferably ovarian cancer, preferably a level of anti-PAR1 antibodies below 3.5 units/ml, more preferably below 3 units/ml, more preferably below 2.7 units/ml, also preferred below 2.5 units/ml is indicative for cancer, preferably ovarian cancer.

Hence, the invention relates to a method for the diagnosis of a cancer selected from the group consisting of ovarian cancer, a solid organ cancer, squamous cell carcinoma of the skin, and metastatic cancer, comprising the steps of (i) determining the level of antibodies against PAR1 in a sample from a subject to be diagnosed, (ii) comparing the determined level in the sample to a control level of antibodies against PAR1 in samples derived from subjects without cancer; wherein a decreased level in the sample from the subject to be diagnosed as compared to the control level is indicative for cancer in the subject selected from the group consisting of ovarian cancer, a solid organ cancer, squamous cell carcinoma of the skin, and metastatic cancer. Further, the invention relates to a method for the diagnosis of ovarian cancer, comprising the steps of (i) determining the level of antibodies against PAR1 in a sample from a subject to be diagnosed, (ii) comparing the determined level in the sample to a control level of antibodies against PAR1 in samples derived from subjects without cancer; wherein a decreased level in the sample from the subject to be diagnosed as compared to the control level is indicative for ovarian cancer in the subject to be diagnosed.

Figure 9:
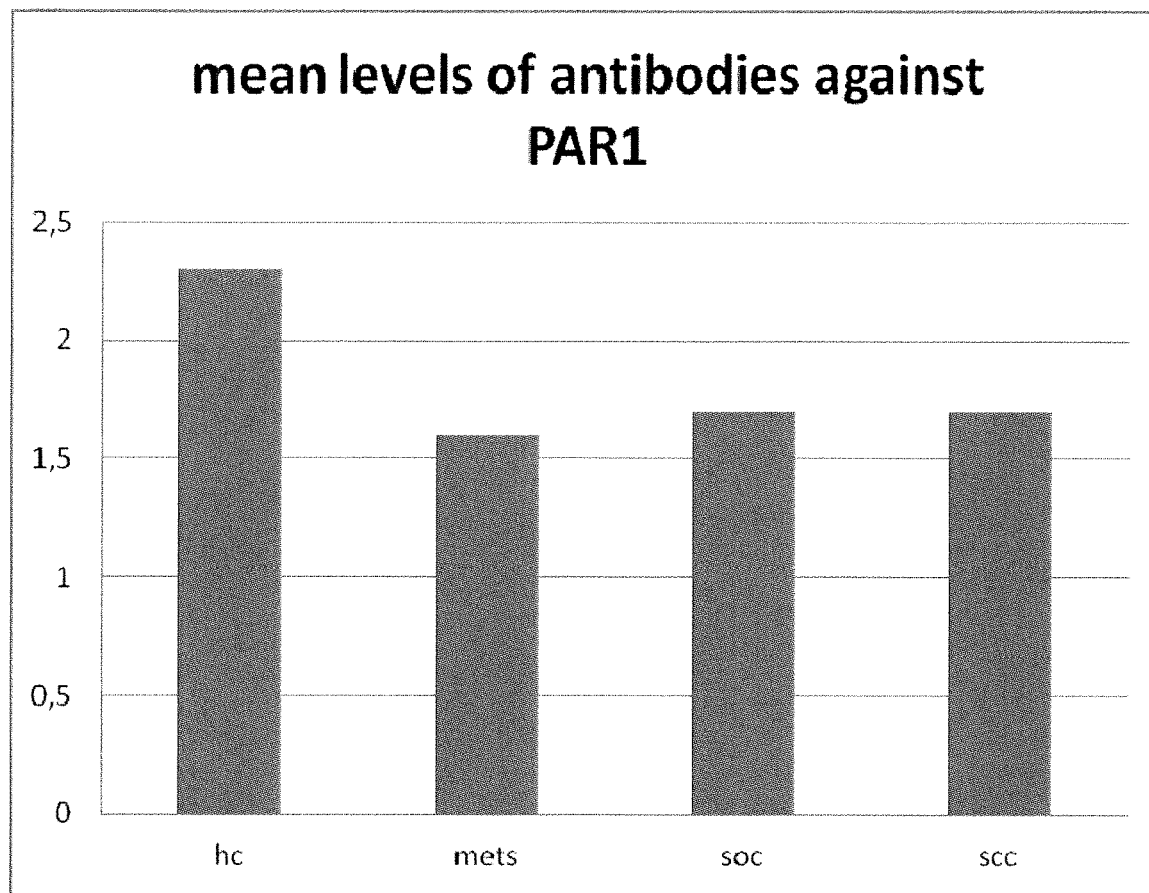
FIG. 9: Comparison of the mean level of anti-PAR1 antibodies (units/ml) in plasma samples of a healthy control group (hc; mean=2.3 units/ml; n=32) to the mean level of anti-PAR1 antibodies in plasma samples patients suffering from metastatic cancer (mets; mean=1.6 units/ml; n=4), solid organ cancer (soc; mean=1.7 units/ml; n=14), and squamous cell cancer of the skin (scc, mean=1.7; n=25).

As can be derived from FIG. 1, the ln of the mean level of PAR1 antibodies in serum samples of patients suffering from ovarian cancer is 0.115 (=1.122 units/ml) and in healthy subjects 1.466 (=4.33 units/ml). FIG. 9 shows that in plasma samples healthy subjects have a mean level of PAR1 antibodies of 2.3, while patients with metastatic cancer show a level of 1.6 units/ml and patients suffering from a solid organ tumor or squamous cell cancer have a PAR1 antibody level in plasma of 1.7 units/ml. The methods according to the present invention, may also be performed by determining the ratios of the levels of the subject to be diagnosed and the control levels. Hence, in one embodiment a level of less than 0.9 fold as compared to the control level from subjects without cancer is indicative for the presence of cancer, preferably a level of less than 0.8 fold, more preferably of less than 0.75 fold. The cancer is preferably a cancer as defined herein. Particularly preferred is ovarian cancer. The skilled person will acknowledge that in case a certain cancer is to be diagnosed, the control level is preferably derived from subjects not having this particular cancer. However, as in all tested cancers the levels are lower than in healthy controls, the control level is preferably derived from subjects not having cancer.

As can be derived from the examples provided herein, the ratio may be even lower for different types of cancers, e.g. ovarian cancer (about 0.26 fold compared to the control level from subjects without cancer). Hence, in one embodiment a level of less than 0.7 fold as compared to the control level from subjects without cancer is indicative for the presence of ovarian cancer. In a further embodiment a level of less than 0.6 fold as compared to the control level from subjects without cancer is indicative for the presence of ovarian cancer, preferably a level of less than 0.3 fold as compared to the control level from subjects without cancer is indicative for the presence of ovarian cancer, in a particular preferred embodiment a level in serum samples of a subject to be diagnosed of less than 0.3 fold as compared to the control level from serum samples of subjects without cancer is indicative for the presence of ovarian cancer.

The inventors unexpectedly found that the level of antibodies against PAR1 in samples of subjects suffering from primary malign ovarian cancer is lower than the level of antibodies against PAR1 in samples of subjects suffering from benign ovarian cancer, the latter levels itself being lower that the levels of antibodies against PAR1 in samples of healthy subjects. This shows that the level of PAR1 is inversely proportional to the grade of ovarian cancer in the subject to be diagnosed. Hence, the present invention also relates to a method for differential diagnosis of cancer comprising the steps of (i) determining the level of antibodies against protease-activated receptor 1 (PAR1) in a sample from a subject to be diagnosed,
(ii) comparing the determined level in the sample to either one or both of a first and second (PAR1) control level,
    a) wherein the first PAR1 antibody control level is derived from subjects suffering from benign cancer, and
    b) wherein the second PAR1 antibody control level derived from subjects suffering from malign cancer,
wherein a decreased level in the sample from the subject to be diagnosed as compared to the first PAR1 antibody control level and/or an equal level as compared to the second PAR1 antibody control level is indicative for malign cancer, preferably primary malign cancer, in the subject, and
wherein an increased level in the sample from the subject to be diagnosed as compared to the second PAR1 antibody control level and/or an equal level as compared to the first PAR1 antibody control level is indicative for a benign cancer in the subject. In a preferred embodiment, ratios of the determined level in the subject to be diagnosed as compared to the one or both PAR1 control levels are calculated. Hence, in one embodiment of the methods for differential diagnosis of a cancer a level of antibodies against PAR1 in the sample from the subject to be diagnosed of less than 0.9 fold as compared to the first PAR1 antibody control level is indicative for malign cancer in said subject to be diagnosed, preferably a level of antibodies against PAR1 in the sample from the subject to be diagnosed of less than 0.5 fold as compared to the first PAR1 antibody control level is indicative for malign cancer in said subject to be diagnosed, more preferably a level of antibodies against PAR1 in the sample from the subject to be diagnosed of less than 0.4 fold as compared to the first PAR1 antibody control level is indicative for malign cancer in said subject to be diagnosed. The term malign cancer preferably refers to primary malign cancer. Likewise, ratios may be determined with respect to the second antibody control level as specified. In such embodiment which may be used in addition or as an alternative to the ratio compared to the first control level, a level of antibodies against PAR1 in the sample from the subject to be diagnosed of more than 1.1 fold as compared to the second PAR1 antibody control level is indicative for benign cancer in said subject to be diagnosed, preferably a level of antibodies against PAR1 in the sample from the subject to be diagnosed of more than 3 fold as compared to the second PAR1 antibody control level is indicative for benign cancer in said subject to be diagnosed, more preferably a level of antibodies against PAR1 in the sample from the subject to be diagnosed of more than 5 fold as compared to the second PAR1 antibody control level is indicative for benign cancer in said subject to be diagnosed.

A preferred cancer in connection with the differential diagnosis is ovarian cancer. Hence, the present invention also relates to a method for differential diagnosis of ovarian cancer comprising the steps of (i) determining the level of antibodies against protease-activated receptor 1 (PAR1) in a sample from a subject to be diagnosed, (ii) comparing the determined level in the sample to either one or both of a first and second (PAR1) control level, a) wherein the first PAR1 antibody control level is derived from subjects suffering from benign ovarian cancer, and b) herein the second PAR1 antibody control level derived from subjects suffering from malign ovarian cancer, preferably primary malign ovarian cancer, wherein a decreased level in the sample from the subject to be diagnosed as compared to the first PAR1 antibody control level and/or an equal level as compared to the second PAR1 antibody control level is indicative for malign ovarian cancer, preferably primary malign ovarian cancer, in the subject, and wherein an increased level in the sample from the subject to be diagnosed as compared to the second PAR1 antibody control level and/or an equal level as compared to the first PAR1 antibody control level is indicative for a benign ovarian cancer in the subject. The subject is preferably a human, preferably a female human, suspected to have or diagnosed as having an ovarian cancer. In a preferred embodiment, ratios of the determined level in the subject to be diagnosed as compared to the one or both PAR1 control levels are calculated. Hence, in one embodiment of the methods for differential diagnosis of a ovarian cancer a level of antibodies against PAR1 in the sample from the subject to be diagnosed of less than 0.9 fold as compared to the first PAR1 antibody control level is indicative for malign ovarian cancer in said subject to be diagnosed, preferably a level of antibodies against PAR1 in the sample from the subject to be diagnosed of less than 0.5 fold as compared to the first PAR1 antibody control level is indicative for malign ovarian cancer in said subject to be diagnosed, more preferably a level of antibodies against PAR1 in the sample from the subject to be diagnosed of less than 0.4 fold as compared to the first PAR1 antibody control level is indicative for malign ovarian cancer in said subject to be diagnosed. The term malign ovarian cancer preferably refers to primary malign ovarian cancer. Likewise, ratios may be determined with respect to the second antibody control level as specified. In such embodiment which may be used in addition or as an alternative to the ratio compared to the first control level, a level of antibodies against PAR1 in the sample from the subject to be diagnosed of more than 1.1 fold as compared to the second PAR1 antibody control level is indicative for benign cancer in said subject to be diagnosed, preferably a level of antibodies against PAR1 in the sample from the subject to be diagnosed of more than 3 fold as compared to the second PAR1 antibody control level is indicative for benign cancer in said subject to be diagnosed, more preferably a level of antibodies against PAR1 in the sample from the subject to be diagnosed of more than 5 fold as compared to the second PAR1 antibody control level is indicative for benign cancer in said subject to be diagnosed.

Malignancy (from Latin male, meaning "badly", and -gnus, meaning "born") is the tendency of a medical condition to become progressively worse. Malignancy familiar as a characterization of cancer. A malignant tumor (interchangeably referred to herein as malignant cancer) contrasts with a benign tumor (interchangeably referred to herein as benign cancer) in that a malignant tumor is not self-limited in its growth, is capable of invading into adjacent tissues, and may be capable of spreading to distant tissues. A benign tumor has none of those properties. Malignancy in cancers is characterized by anaplasia, invasiveness, and metastasis. Malignant tumors are also characterized by genome instability, so that cancers, as assessed by whole genome sequencing, frequently have between 10,000 and 100,000 mutations in their entire genomes.

The inventors also found that differential diagnosis as to the grade (differentiation; grading) of cancer, particularly a solid organ cancer like ovarian cancer is possible when using the method according to the present invention. Hence, the present invention also relates to a method for differential diagnosis of a cancer, preferably a solid organ cancer, comprising the steps of
  (i) determining the level of antibodies against PAR1 in a sample from a subject to be diagnosed,
  (ii) comparing the determined level in the sample to either one or both of a first and second PAR1 antibody control level,
    a) wherein the first PAR1 antibody control level is derived from subjects suffering from a cancer classified as Grade II or Grade III cancer, preferably Grade II or Grade III solid organ cancer, and
    b) wherein the second PAR1 antibody control level is derived from a subject suffering from an cancer classified as Grade I cancer, preferably Grade I solid organ cancer,
  wherein a increased level in the sample from the subject to be diagnosed as compared to the first PAR1 antibody control level and/or an equal level as compared to the second PAR1 antibody control level is indicative for Grade I cancer, preferably Grade I solid organ cancer, in said subject to be diagnosed, and wherein an decreased level in the sample from the subject to be diagnosed as compared to the second PAR1 antibody control level and/or an equal level as compared to the first PAR1 antibody control level is indicative for Grade II or Grade III cancer, preferably Grade II or III solid organ cancer, in said subject to be diagnosed. This method in one embodiment is a method for differentiating between Grade I and Grade II or Grade III cancer, preferably Grade I solid organ cancer. It is apparent that thereby the present invention provides a method for differentiating between histological grades of tumors without the necessity of surgical intervention. Hence, in one embodiment of the method for differential diagnosis, the method is preformed without surgical treatment and histological analysis. However, the present invention may also be used to assist histological analysis and may hence be used in parallel. Nevertheless, surgical biopsy and histological analysis are not part of the invention. The levels indicative may be determined using the method above, i.e. using control levels, which may be determined by the skilled person when considering the disclosure of the present invention.

The subject to be differentially diagnosed is preferably a human, preferably a human suspected to suffer from cancer or which has been diagnosed as having cancer, preferably a solid organ cancer. For the embodiments relating to differential diagnosis of ovarian cancer as disclosed herein, the subject to be diagnosed is preferably a female human suspected to suffer from ovarian cancer or which has been diagnosed as having ovarian cancer.

The method for differential diagnosis of cancer in terms of grading may also be conducted using ratios. As can be derived from FIG. 2, the ln of the mean level of PAR1 antibodies in patients suffering from a Grade I cancer is 1.082 (down to 0.5 when considering the standard error of mean) (=2.95 units/ml; down to 1.65 when considering the standard error of mean) and in patients suffering from Grade II or III cancer the ln of the mean level is 0.081 (=1.08 units/ml), i.e. with ratios from 0.65 fold to 0.37 fold, or 1.53 fold to 2.73 fold, respectively. Hence, in one embodiment of the methods for differential diagnosis of a cancer a level of antibodies against PAR1 in the sample from the subject to be diagnosed of less than 0.9 fold as compared to the second PAR1 antibody control level is indicative for Grade II or Grade III cancer in said subject to be diagnosed, preferably a level of antibodies against PAR1 in the sample from the subject to be diagnosed of less than 0.7 fold as compared to the second PAR1 antibody control level is indicative for Grade II or Grade III cancer in said subject to be diagnosed, more preferably a level of antibodies against PAR1 in the sample from the subject to be diagnosed of less than 0.5 fold as compared to the second PAR1 antibody control level is indicative for Grade II or Grade III cancer in said subject to be diagnosed; even more preferred a level of antibodies against PAR1 in the sample from the subject to be diagnosed of less than 0.4 fold as compared to the second PAR1 antibody control level is indicative for Grade II or Grade III cancer in said subject to be diagnosed. Likewise, ratios may be determined with respect to the first antibody control level. In such embodiment which may be used in addition or as an alternative to the ratio of the second control level, a level of antibodies against PAR1 in the sample from the subject to be diagnosed of more than 1.1 fold as compared to the first PAR1 antibody control level is indicative for Grade I cancer in said subject to be diagnosed, preferably a level of antibodies against PAR1 in the sample from the subject to be diagnosed of more than 1.5 fold as compared to the first PAR1 antibody control level is indicative for Grade I cancer in said subject to be diagnosed, more preferably a level of antibodies against PAR1 in the sample from the subject to be diagnosed of more than 2.0 fold as compared to the first PAR1 antibody control level is indicative for Grade I cancer in said subject to be diagnosed, even more preferred a level of antibodies against PAR1 in the sample from the subject to be diagnosed of more than 2.5 fold as compared to the first PAR1 antibody control level is indicative for Grade I cancer in said subject to be diagnosed.

Hence, the present invention also relates to a method for differential diagnosis of ovarian cancer comprising the steps of
(i) determining the level of antibodies against protease-activated receptor 1 (PAR1) in a sample from a subject to be diagnosed,
(ii) comparing the determined level in the sample to either one or both of a first and second (PAR1) control level,
   a) wherein the first PAR1 antibody control level is derived from subjects suffering from an ovarian cancer classified as Grade II or Grade III ovarian cancer, and
   b) wherein the second PAR1 antibody control level is derived from a subject suffering from an ovarian cancer classified as Grade I ovarian cancer
wherein a increased level in the sample from the subject to be diagnosed as compared to the first PAR1 antibody control level and/or an equal level as compared to the second PAR1 antibody control level is indicative for Grade I ovarian cancer in said subject to be diagnosed, and wherein an decreased level in the sample from the subject to be diagnosed as compared to the second PAR1 antibody control level and/or an equal level as compared to the first PAR1 antibody control level is indicative for Grade II or Grade III ovarian cancer in said subject to be diagnosed. This method in one embodiment is a method for differentiating between Grade I and Grade II or Grade III ovarian cancer. It is apparent that thereby the present invention provides a method for differentiating between histological grades of tumors without the necessity of surgical intervention. Hence, in one embodiment of the method for differential diagnosis, the method is preformed without surgical treatment and histological analysis. However, the present invention may also be used to assist histological analysis and may hence be used in parallel. Nevertheless, surgical biopsy and histological analysis are not part of the invention. The levels indicative may be determined using the method above, i.e. using control levels, which may be determined by the skilled person when considering the disclosure of the present invention. However, in a preferred embodiment a level of less than 2.7 units/ml is indicative for Grade II or Grade III ovarian cancer and levels of 2.7 units/ml or more are indicative for Grade I ovarian cancer. In a further preferred embodiment a level of less than 2.5 units/ml is indicative for Grade II or Grade III ovarian cancer and levels of 2.5 units/ml or more are indicative for Grade I ovarian cancer. In a yet a further preferred embodiment a level of less than 2.0 units/ml is indicative for Grade II or Grade III ovarian cancer and levels of 2.0 units/ml or more are indicative for Grade I ovarian cancer. In an even further preferred embodiment a level of less than 1.5 units/ml is indicative for Grade II or Grade III ovarian cancer and levels of 1.5 units/ml or more are indicative for Grade I ovarian cancer.

As outlined above ratios are well suited for the methods according to the present invention. Hence, in one embodiment of the methods for differential diagnosis of ovarian cancer a level of antibodies against PAR1 in the sample from the subject to be diagnosed of less than 0.9 fold as compared to the second PAR1 antibody control level is indicative for Grade II or Grade III ovarian cancer in said subject to be diagnosed, preferably a level of antibodies against PAR1 in the sample from the subject to be diagnosed of less than 0.7 fold as compared to the second PAR1 antibody control level is indicative for Grade II or Grade III ovarian cancer in said subject to be diagnosed, more preferably a level of antibodies against PAR1 in the sample from the subject to be diagnosed of less than 0.5 fold as compared to the second PAR1 antibody control level is indicative for Grade II or Grade III ovarian cancer in said subject to be diagnosed; even more preferred a level of antibodies against PAR1 in the sample from the subject to be diagnosed of less than 0.4 fold as compared to the second PAR1 antibody control level is indicative for Grade II or Grade III ovarian cancer in said subject to be diagnosed. Likewise, ratios may be determined with respect to the first antibody control level. In such embodiment which may be used in addition or as an alternative to the ratio of the second control level, a level of antibodies against PAR1 in the sample from the subject to be diagnosed of more than 1.1 fold as compared to the first PAR1 antibody control level is indicative for Grade I ovarian cancer in said subject to be diagnosed, preferably a level of antibodies against PAR1 in the sample from the subject to be diagnosed of more than 1.5 fold as compared to the first PAR1 antibody control level is indicative for Grade I ovarian cancer in said subject to be diagnosed, more preferably a level of antibodies against PAR1 in the sample from the subject to be diagnosed of more than 2.0 fold as compared to the first PAR1 antibody control level is indicative for Grade I ovarian cancer in said subject to be diagnosed, even more preferred a level of antibodies against PAR1 in the sample from the subject to be diagnosed of more than 2.5 fold as compared to the first PAR1 antibody control level is indicative for Grade I ovarian cancer in said subject to be diagnosed.

Furthermore, the inventors found that it is possible to differentiate between high grade serous ovarian cancer (HGSOC) (histological Figo Stage II and III and deriving from the fallopian tube) and low grade serous ovarian cancer (LGSOC) (histological Figo Stage I and derived from borderline tumors) by the levels of anti-PAR1 antibodies in samples of subjects suffering from ovarian cancer. This provides for a method of further differentiating ovarian cancer. Hence, the present invention also relates to a method for differential diagnosis of ovarian cancer comprising the steps of
   (i) determining the level of antibodies against protease-activated receptor 1 (PAR1) in a sample from a subject to be diagnosed,
   (ii) comparing the determined level in the sample to either one or both of a first and second PAR1 antibody control level,
      a) wherein the first PAR1 antibody control level is derived from subjects suffering from high grade serous ovarian cancer (HGSOC), and
      b) wherein the second PAR1 antibody control level is derived from a subject suffering from low grade serous ovarian cancer (LGSOC),
wherein a increased level in the sample from the subject to be diagnosed as compared to the first PAR1 antibody control level and/or an equal level as compared to the second PAR1 antibody control level is indicative for LGSOC in said subject to be diagnosed, and wherein an decreased level in the sample from the subject to be diagnosed as compared to the second PAR1 antibody control level and/or an equal level as compared to the first PAR1 antibody control level is indicative for HGSOC in said subject to be diagnosed. It is apparent that thereby the present invention provides a method for differentiating between histological grades of tumors without the necessity of surgical intervention. Hence, in one embodiment of the method for differential diagnosis, the method is preformed without surgical treatment and histological analysis. However, the present invention may also be used to assist histological analysis and may hence be used in parallel. Nevertheless, surgical biopsy and histological analysis are not part of the invention. The levels indicative may be determined using the method above, i.e. using control levels, which may be determined by the skilled person when considering the disclosure of the present invention.

However, in a preferred embodiment a level of less than 2.7 units/ml is indicative for HGSOC and levels of 2.7 units/ml or more are indicative for LGSOC. In a further preferred embodiment a level of less than 2.5 units/ml is indicative for HGSOC and levels of 2.5 units/ml or more are indicative for Grade I ovarian cancer. In a yet a further preferred embodiment a level of less than 2.0 units/ml is indicative for HGSOC and levels of 2.0 units/ml or more are indicative for LGSOC. In an even further preferred embodiment a level of less than 1.5 units/ml is indicative for HGSOC and levels of 1.5 units/ml or more are indicative for LGSOC.

As outlined above ratios are well suited for the methods according to the present invention. As can be derived from FIG. 3, the ln of the mean level of PAR1 antibodies in patients suffering from a HGSOC is 0.076 (=1.08 units/ml) and in patients suffering from LGSOC the ln of the mean level is 1.082 (down to 0.5 when considering the standard error of mean) (=2.95 units/ml; down to 1.65 units/ml when considering the standard error of mean), i.e. with ratios from 0.65 fold to 0.4 fold, or 1.29 fold to 2.74 fold, respectively. Hence, in one embodiment of the methods for differential diagnosis in terms of differentiating between HGSOC and LGSOC a level of antibodies against PAR1 in the sample from the subject to be diagnosed of less than 0.9 fold as compared to the second PAR1 antibody control level is indicative for HGSOC in said subject to be diagnosed, preferably a level of antibodies against PAR1 in the sample from the subject to be diagnosed of less than 0.7 fold as compared to the second PAR1 antibody control level is indicative for HGSOC in said subject to be diagnosed, more preferably a level of antibodies against PAR1 in the sample from the subject to be diagnosed of less than 0.5 fold as compared to the second PAR1 antibody control level is indicative for HGSOC in said subject to be diagnosed; even more preferred a level of antibodies against PAR1 in the sample from the subject to be diagnosed of less than 0.45 fold as compared to the second PAR1 antibody control level is indicative HGSOC in said subject to be diagnosed. Likewise, ratios may be determined with respect to the first antibody control level. In such embodiment which may be used in addition or as an alternative to the ratio of the second control level, a level of antibodies against PAR1 in the sample from the subject to be diagnosed of more than 1.1 fold as compared to the first PAR1 antibody control level is indicative for LGSOC in said subject to be diagnosed, preferably a level of antibodies against PAR1 in the sample from the subject to be diagnosed of more than 1.2 fold as compared to the first PAR1 antibody control level is indicative for LGSOC in said subject to be diagnosed, more preferably a level of antibodies against PAR1 in the sample from the subject to be diagnosed of more than 2.0 fold as compared to the first PAR1 antibody control level is indicative for LGSOC in said subject to be diagnosed, even more preferred a level of antibodies against PAR1 in the sample from the subject to be diagnosed of more than 2.5 fold as compared to the first PAR1 antibody control level is indicative for LGSOC in said subject to be diagnosed.

The samples in connection with the methods for differential diagnosis of cancer are preferably a bodily fluid, preferably a blood sample, more preferred selected from a serum sample and a plasma sample. The detection with respect of differential diagnosis in the enclosed examples has been conducted on serum samples. However, the skilled person will acknowledge that the method may also be performed on other type of samples. It is preferred that the samples in which the levels are determined are of the same type as the samples to which the controls refer. In one particular embodiment of the methods for differential diagnosis the sample is a serum sample.

The invention also relates to a method for determining whether a subject being treated or to be treated for cancer with a drug will respond to said treatment comprising the steps of
(i) determining the level of antibodies against protease-activated receptor 1 (PAR1) in a sample from said subject being treated or to be treated; and
(ii) comparing the determined level in the sample to either one or both of a first and second PAR1 antibody control level,
  a) wherein the first PAR1 antibody control level is derived from subjects responding to said treatment, and
  b) wherein the second PAR1 antibody control level is derived from subjects not responding to said treatment,
wherein a decreased level in the sample from the subject being treated or to be treated as compared to the first PAR1 antibody control level and/or an equal level as compared to the second PAR1 antibody control level is indicative for a non-response of said subject to said treatment, and wherein an increased level in the sample from the subject being treated or to be treated as compared to the second PAR1 antibody control level and/or an equal level as compared to the first PAR1 antibody control level is indicative for a response of said subject to said treatment. In a preferred embodiment of the invention the subject is to be treated, i.e. the method to determine response of a subject is performed before the onset of treatment. In a preferred embodiment the drug is an angiogenesis inhibitor or an inhibitor of EGFR activity according to the present invention. Ratios may be applied when comparing the determined levels to the control levels. Hence, in one embodiment of the method for determining whether a subject being treated or to be treated for cancer with a drug will respond to said treatment, a level of antibodies against PAR1 in the sample from the subject to be treated of less than 0.9 fold as compared to the first PAR1 antibody control level is indicative for a non-response of said subject to said treatment, preferably a level of antibodies against PAR1 in the sample from the subject to be treated of less than 0.8 fold as compared to the first PAR1 antibody control level is indicative for a non-response of said subject to said treatment, further preferred a level of antibodies against PAR1 in the sample from the subject to be treated of less than 0.7 fold as compared to the first anti-PAR1 control level is indicative for a non-response of said subject to said treatment. Likewise, ratios may be determined for the response. In such embodiment a level of antibodies against PAR1 in the sample from the subject to be treated of more than 1.1 fold as compared to the second PAR1 antibody control level is indicative for a response of said subject to said treatment, preferably a level of antibodies against PAR 1 in the sample from the subject to be treated of more than 1.3 fold as compared to the second PAR1 antibody control level is indicative for a response of said subject to said treatment, further preferred a level of antibodies against PAR1 in the sample from the subject to be treated of more than 1.5 fold as compared to the second anti-PAR1 control level is indicative for a response of said subject to said treatment.

The drug is preferably a drug as defined herein below. In a preferred embodiment the drug used for the treatment of cancer is an angiogenesis inhibitor or an inhibitor of EGFR activity. Representative drugs from both preferred groups have been tested and their predictive and prognostic value has been confirmed in the examples provided herewith. The two tested representative drugs were bevacizumab and panitumumab. Hence, the invention also relates to a method for determining whether a subject being treated or to be treated for cancer with an angiogenesis inhibitor or an inhibitor of EGFR activity will respond to said treatment comprising the steps of (i) determining the level of antibodies against protease-activated receptor 1 (PAR1) in a sample from said subject being treated or to be treated; and (ii) comparing the determined level in the sample to either one or both of a first and second PAR1 antibody control level, a) wherein the first PAR1 antibody control level is derived from subjects responding to said treatment, and b) wherein the second PAR1 antibody control level is derived from subjects not responding to said treatment, wherein a decreased level in the sample from the subject being treated or to be treated as compared to the first PAR1 antibody control level and/or an equal level as compared to the second PAR1 antibody control level is indicative for a non-response of said subject to said treatment, and wherein an increased level in the sample from the subject being treated or to be treated as compared to the second PAR1 antibody control level and/or an equal level as compared to the first PAR1 antibody control level is indicative for a response of said subject to said treatment. As also instantly derivable from the present disclosure for the skilled person the ratios between anti PAR1 levels or responders to non responders are similar for the both preferred groups of drugs. Hence, in one embodiment of the method for determining whether a subject being treated or to be treated for cancer with an angiogenesis inhibitor or an inhibitor of EGFR activity will respond to said treatment, a level of antibodies against PAR1 in the sample from the subject to be treated of less than 0.9 fold as compared to the first PAR1 antibody control level is indicative for a non-response of said subject to said treatment with an angiogenesis inhibitor or an inhibitor of EGFR activity, preferably a level of antibodies against PAR1 in the sample from the subject to be treated of less than 0.8 fold as compared to the first PAR1 antibody control level is indicative for a non-response of said subject to said treatment with an angiogenesis inhibitor or an inhibitor of EGFR activity, further preferred a level of antibodies against PAR1 in the sample from the subject to be treated of less than 0.7 fold as compared to the first anti-PAR1 control level is indicative for a non-response of said subject to said treatment with an angiogenesis inhibitor or an inhibitor of EGFR activity. Likewise, ratios may be determined for the response. In such embodiment a level of antibodies against PAR1 in the sample from the subject to be treated of more than 1.1 fold as compared to the second PAR1 antibody control level is indicative for a response of said subject to said treatment with an angiogenesis inhibitor or an inhibitor of EGFR activity, preferably a level of antibodies against PAR 1 in the sample from the subject to be treated of more than 1.3 fold as compared to the second PAR1 antibody control level is indicative for a response of said subject to said treatment with an angiogenesis inhibitor or an inhibitor of EGFR activity, further preferred a level of antibodies against PAR1 in the sample from the subject to be treated of more than 1.5 fold as compared to the second anti-PAR1 control level is indicative for a response of said subject to said treatment with an angiogenesis inhibitor or an inhibitor of EGFR activity. Preferred angiogenesis inhibitors are disclosed herein. One particular preferred angiogenesis inhibitor is bevacizumab. Preferred inhibitors of EGFR activity are disclosed herein. One particular preferred inhibitor of EGFR activity is panitumumab.

In one embodiment the invention also relates to a method for determining whether a subject being treated or to be treated for cancer with bevacizumab will respond to said treatment comprising the steps of (i) determining the level of antibodies against protease-activated receptor 1 (PAR1) in a sample from said subject being treated or to be treated; and (ii) comparing the determined level in the sample to either one or both of a first and second PAR1 antibody control level, a) wherein the first PAR1 antibody control level is derived from subjects responding to said treatment, and b) wherein the second PAR1 antibody control level is derived from subjects not responding to said treatment, wherein a decreased level in the sample from the subject being treated or to be treated as compared to the first PAR1 antibody control level and/or an equal level as compared to the second PAR1 antibody control level is indicative for a non-response of said subject to said treatment, and wherein an increased level in the sample from the subject being treated or to be treated as compared to the second PAR1 antibody control level and/or an equal level as compared to the first PAR1 antibody control level is indicative for a response of said subject to said treatment. In one embodiment of the method for determining whether a subject being treated or to be treated for cancer with bevacizumab will respond to said treatment, a level of antibodies against PAR1 in the sample from the subject to be treated of less than 0.9 fold as compared to the first PAR1 antibody control level is indicative for a non-response of said subject to said treatment with bevacizumab, preferably a level of antibodies against PAR1 in the sample from the subject to be treated of less than 0.7 fold as compared to the first PAR1 antibody control level is indicative for a non-response of said subject to said treatment with bevacizumab, further preferred a level of antibodies against PAR1 in the sample from the subject to be treated of less than 0.6 fold as compared to the first anti-PAR1 control level is indicative for a non-response of said subject to said treatment with bevacizumab. Likewise, ratios may be determined for the response. In such embodiment a level of antibodies against PAR1 in the sample from the subject to be treated of more than 1.1 fold as compared to the second PAR1 antibody control level is indicative for a response of said subject to said treatment with bevacizumab, preferably a level of antibodies against PAR 1 in the sample from the subject to be treated of more than 1.5 fold as compared to the second PAR1 antibody control level is indicative for a response of said subject to said treatment with bevacizumab, further preferred a level of antibodies against PAR1 in the sample from the subject to be treated of more than 1.65 fold as compared to the second anti-PAR1 control level is indicative for a response of said subject to said treatment with bevacizumab.

In one embodiment the invention also relates to a method for determining whether a subject being treated or to be treated for cancer with panitumumab will respond to said treatment comprising the steps of (i) determining the level of antibodies against protease-activated receptor 1 (PAR1) in a sample from said subject being treated or to be treated; and (ii) comparing the determined level in the sample to either one or both of a first and second PAR1 antibody control level, a) wherein the first PAR1 antibody control level is derived from subjects responding to said treatment, and b) wherein the second PAR1 antibody control level is derived from subjects not responding to said treatment, wherein a decreased level in the sample from the subject being treated or to be treated as compared to the first PAR1 antibody control level and/or an equal level as compared to the second PAR1 antibody control level is indicative for a non-response of said subject to said treatment, and wherein an increased level in the sample from the subject being treated or to be treated as compared to the second PAR1 antibody control level and/or an equal level as compared to the first PAR1 antibody control level is indicative for a response of said subject to said treatment. In one embodiment of the method for determining whether a subject being treated or to be treated for cancer with panitumumab will respond to said treatment, a level of antibodies against PAR1 in the sample from the subject to be treated of less than 0.9 fold as compared to the first PAR1 antibody control level is indicative for a non-response of said subject to said treatment with panitumumab, preferably a level of antibodies against PAR1 in the sample from the subject to be treated of less than 0.8 fold as compared to the first PAR1 antibody control level is indicative for a non-response of said subject to said treatment with panitumumab, further preferred a level of antibodies against PAR1 in the sample from the subject to be treated of less than 0.7 fold as compared to the first anti-PAR1 control level is indicative for a non-response of said subject to said treatment with panitumumab. Likewise, ratios may be determined for the response. In such embodiment a level of antibodies against PAR1 in the sample from the subject to be treated of more than 1.1 fold as compared to the second PAR1 antibody control level is indicative for a response of said subject to said treatment with panitumumab, preferably a level of antibodies against PAR 1 in the sample from the subject to be treated of more than 1.25 fold as compared to the second PAR1 antibody control level is indicative for a response of said subject to said treatment with panitumumab, further preferred a level of antibodies against PAR1 in the sample from the subject to be treated of more than 1.5 fold as compared to the second anti-PAR1 control level is indicative for a response of said subject to said treatment with panitumumab.

As outlined before the response or non-response of a subject to a treatment can at late stages been evaluated based on mortality, progression or relapse of cancer. Hence, in one embodiment of the present invention, the method for determining whether a subject being treated or to be treated for cancer with a drug will respond to said treatment is a method for prediction of risk stratification for relapse of cancer and/or mortality and/or progression of cancer. Therefore, the present invention also relates to a method for the prediction of risk stratification for relapse of cancer and/or mortality and/or progression of cancer in a subject being treated or to be treated for cancer with a drug, the method comprising the steps of (i) determining the level of antibodies against protease-activated receptor 1 (PAR1) in a sample from said subject to be treated or being treated with an angiogenesis inhibitor; and (ii) comparing the determined level in the sample to either one or both of a first and a second PAR1 antibody control level, a) wherein the first PAR1 antibody control level is derived from subjects not showing relapse or progression of cancer or mortality or after treatment with said drug, and b) wherein the second PAR1 antibody control level is derived from subjects showing relapse or progression of cancer or mortality after treatment with said drug, wherein a decreased level in the sample from the subject being treated or to be treated as compared to the first PAR1 antibody control level and/or an equal level as compared to the second PAR1 antibody control level is indicative for relapse or progression of cancer or mortality in the subject, and wherein a increased level in the sample from the subject being treated or to be treated as compared to the second PAR1 antibody control level and/or an equal level as compared to the first PAR1 antibody control level is indicative for no relapse, no progression and no mortality in the subject. All embodiments herein, in particular those of the method for determining whether a subject being treated or to be treated for cancer with a drug will respond to said treatment apply also to the method for the prediction of risk stratification for relapse of cancer and/or mortality and/or progression of cancer in a subject being treated or to be treated for cancer with a drug As also outlined herein, the invention provides a method for determining whether a patient suffers from cancer or not, preferably ovarian cancer. Hence, in one embodiment of the outlined methods for diagnosis and differential diagnosis according to the present invention may furthermore include the comparison of the determined level from the subject to be diagnosed to a further control level derived from a subject who does not suffer from cancer, preferably the subject from which this control level is derived is proven cancer free, preferably proven free of EGFR or EGF associated cancer, preferably cancer free. In this embodiment the subject to be diagnosed may be pre-classified as suffering from cancer, preferably epithelial cancer, more preferably ovarian cancer, if the levels determined in the subject to be diagnosed are decreased as compared to the control level derived from subject not suffering from cancer.

Figure 8:
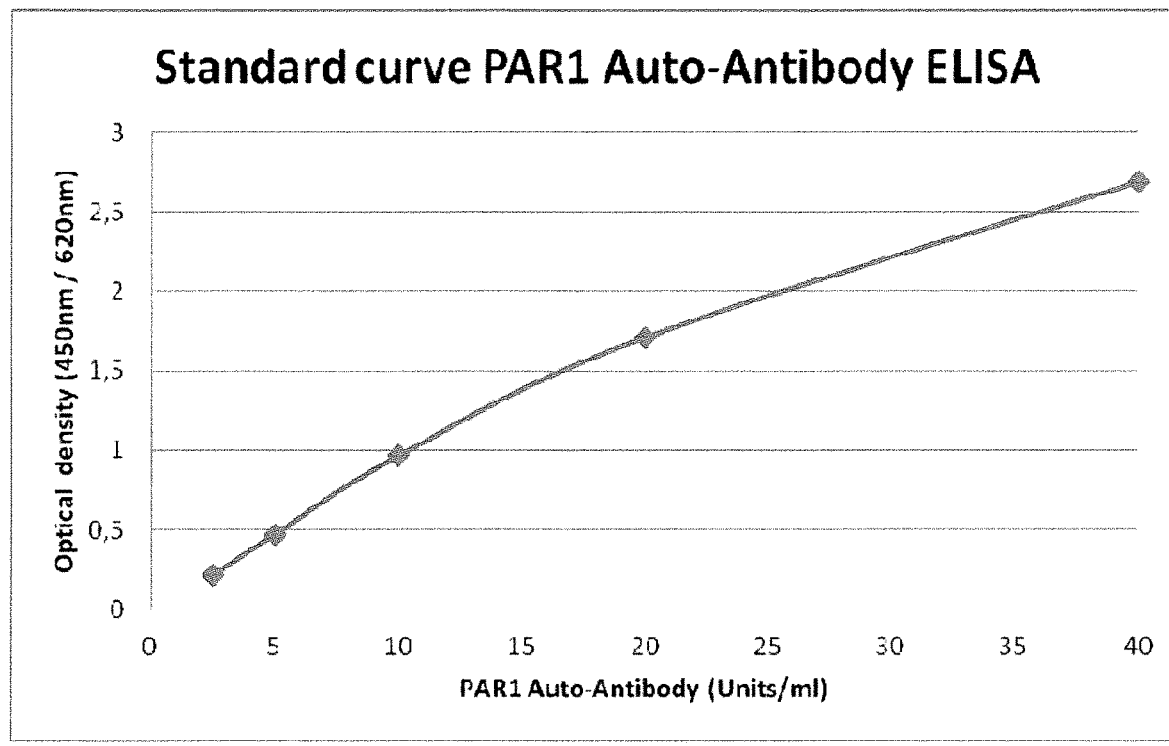
FIG. 8: Standard curve of the PAR1-Auto-Antibody ELISA

As outlined herein, the levels of PAR1 antibodies in samples of the patient to be diagnosed and treated or to be treated are compared with the control groups as defined herein. However, in one embodiment the levels are compared to fixed values, i.e. thresholds under or over which a certain diagnosis, or prognosis of response is given. To this end, unit-standards may be applied. The present inventors set out such standard for the PAR1 using serum samples from systemic sclerosis patients. Systemic sclerosis patients are known to have high levels of autoimmune antibodies in general. Hence, the inventors took a serum sample of a systemic sclerosis patient. However, it will be acknowledged by the skilled person that also other samples may be taken to set a different standard, e.g. samples of healthy subjects, samples of cancer patients. Nevertheless the principle of generating a standard (units) is the same in any case and are exemplified herein using serum samples of systemic sclerosis patients. In the context of the present invention "units/ml", unless specified otherwise, refers to the concentration of antibodies standardised as exemplified herein. Hence, in one embodiment of the present invention 40 units/ml refers to a dilution of 1:100 of a serum sample of systemic sclerosis patients. The serum sample may be derived from a single patient or of a cohort of a plurality of patients, e.g. a cohort of 200 patients suffering from systemic sclerosis. The present inventors found that the concentration of PAR1 antibodies in samples of systemic sclerosis do not differ by more than about 10%, showing such standard being reproducible. In one preferred embodiment the standard for the concentrations of the autoimmune antibodies is generated in the following way: a serum sample of a systemic sclerosis patient (or a larger cohort) is diluted (a) 1:100 for standard point 40 Units/ml, (b) 1:200 for standard point 20 Units/ml, (c) 1:400 for standard point 10 Units/ml, (d) 1:800 for standard point 5 Units/ml and (e) 1:1600 for standard point 2.5 Units/ml. These standards are then used for the immunoassay chosen, e.g. ELISA, and then correlated with the respective read-out value, e.g. for ELISA optical density at 450 nm/optical density at 620 nm. A typical standard curve of a PAR1 auto-antibody ELISA is shown in FIG. 8. Nevertheless, the skilled person will readily understand that it may also be possible to standardize the levels of PAR1-autoantibodies using different samples, e.g samples of healthy subjects or cancer patients. However, it has also been found that ratios may be determined as outlined herein. In such case, it is preferred that the determined levels and the control levels are determined using the same standard, e.g. the one outlined herein or any other standard accessible to the skilled person.

"equal" level in context with the present invention means that the levels differ by not more than ±10%, preferably by not more than ±5%, more preferably by not more than ±2%. "Decreased" or "increased" level in the context of the present invention mean that the levels differ by more than 10%, preferably by more than 15%, preferably more than 20%. In terms of ratios, equal preferably relates to ratios between 0.9 fold to 1.1 fold, preferably between 0.95 fold to 1.05 fold, more preferably 0.98 fold to 1.02 fold.

It will be readily understood by the skilled person that the control levels from subjects having the desired disease or response and to which the determined levels are compared to, are not necessarily determined in parallel but may be represented by previously determined levels. Nevertheless, control levels may be determined in parallel. The skilled person with the disclosure of the present invention and his knowledge is able to determine such levels, as will be outlined herein below. Hence, the control levels of the present invention may be previously defined thresholds. Preferred thresholds and respective ratios are disclosed herein.

In the context of the present invention the terms "PAR1" and "PAR1-receptor" equally relate to the "protease-activated receptor 1" (also known as "coagulation factor II receptor", "thrombin receptor", "F2R", "TR" and "CF2R").

Protease-activated receptors (PARs) are involved in a number of essential biological processes such as blood clotting, regulation of vascular tone and vascular permeability, motility of the gastrointestinal tract, perception of pain, inflammatory response (including arthritis), angiogenesis, muscle growth and bone cell differentiation and proliferation. PARs are members of the 7-trans-membrane-helix G protein-coupled receptor (GPCR) super family and are activated by cleavage of part of their extracellular domain. They are expressed throughout the body. Particularly high expression occurs in platelets, but also on endothelial cells, myocytes and neurons. Expression of PAR on cells is influenced by the presence of cytokines such as TNFα.

Four different types of PAR receptors have been identified, designated PAR1, PAR2, PAR3 and PAR4. PAR1 and PAR2 are the best studied among the PAR-type receptors and share a sequence homology of 30%.

PAR receptors are activated by the action of serine proteases such as thrombin (PAR 1, 3 and 4) and trypsin (PAR 2). PAR 1 and PAR2 are both activated by Factor Xa, PAR2 is also activated by proteinase III. These proteases cleave the N-terminus of the receptor, which in turn acts as a tethered ligand. In the cleaved state, part of the receptor itself acts as the agonist, causing a physiological response. Most of the PAR-type receptors act through the actions of G-proteins, Raf/Ras activation and calcium signaling to cause cellular actions. Inactivation of PAR receptors is, inter alia, mediated by elastases and proteases.

A number of agonist and antagonist of PAR have been developed, however, their effects on activation and inhibition of the receptors is highly dependent on the type of cells carrying the respective receptor, the surrounding environment of these cells and ligand concentration.

PAR1-deficient mouse embryos were shown to have a 50% intrauterine lethality. In the surviving knockout mice, an increased deposition of extracellular matrix components in the tissues, infiltration of lymphocytes in the lungs and the occurrence of membranoproliferative glomerulonephritis have been observed. PAR2-deficient mice have shown to exhibit a disturbed leukocyte migration and suffer from nephritis, arthritis and pneumonia.

In the context of the immunoassays of the present invention the "PAR1-receptor" may be present in its natural cellular environment and can be used together with the material associated with the receptor in its natural state as well as in isolated form with respect to its primary, secondary and tertiary structures. The PAR1-receptor is well known to those skilled in the art. The receptor is preferably used in isolated form, i.e. essentially free of other proteins, lipids, carbohydrates or other substances naturally associated with the receptor. "Essentially free of" means that the receptor is at least 75%, preferably at least 85%, more preferably at least 95% and especially preferably at least 99% free of other proteins, lipids, carbohydrates or other substances naturally associated with the receptor.

In connection with the present invention, the naturally occurring receptor as well as all modifications, mutants or derivatives of the PAR1-receptor can be used. Similarly, a PAR1-receptor produced by means of recombinant techniques, which receptor includes amino acid modifications, such as inversions, deletions, insertions, additions etc. can be used according to the invention provided that this part of the essential function of the PAR1-receptor is present, namely the capability of binding antibodies. The PAR1-receptor being used may also comprise exceptional amino acids and/or modifications of such as alkylation, oxidation, thiol-modification, denaturation, oligomerization and the like. The receptor can also be synthesized by chemical means. According to the invention the PAR1-receptor particularly can be a protein and/or peptide or a fusion protein, which in addition to other proteins, peptides or fragments thereof, includes the PAR1-receptor as a whole or in part. Using conventional methods, peptides or polypeptides of the PAR1-receptor which have functionally analogs, analogous properties can be determined by those skilled in the art. For example such polypeptides or peptides have 50-60%, 70% or 80%, preferably 90%, more preferably 95%, and most preferably 98% homology to peptides identified as PAR1-receptor, and said homology can be determined, e.g. by means of Smith-Waterman homology search algorithm, using the MPFRCH program (Oxford Molecular), for example.

The term "peptide" or "polypeptide" of an PAR1-receptor used in the present invention, comprises also molecules differing from the original sequence by deletion(s), insertion(s), substitution(s) and/or other modifications well known in the prior art and/or comprising a fragment of the original amino acid molecule, the PAR1-receptor still exhibiting the properties mentioned above. Such a peptide has preferably at least a length of 100 amino acid residues but may also be shorter, e.g. at least 12, 15, 20 or 25 amino acid residues in length. Also included are allele variants and modifications. Methods of producing the above changes in the amino acid sequence are well known to those skilled in the art and have been described in the standard textbooks of molecular biology, e.g. Sambrook et al., supra. Those skilled in the art will also be able to determine whether a PAR1-receptor, thus, modified still has the properties mentioned above. The amino acid sequence of two isoforms of the PAR1 receptor is given below and in the attached SEQ ID NO:1 and SEQ ID NO:2. Residues 42 to 425 in SEQ ID NO:1 and SEQ ID NO:2 relate to the amino acid sequence of the mature receptor, while residues 1 to 26 relate to a signal peptide and residues 27 to 41 are removed from the receptor proprotein upon activation. Hence, PAR1 in the context of the present invention preferably relates to the mature PAR1 receptor corresponding to residues 42 to 425 of SEQ ID NO:1 or SEQ ID NO:2. The receptor may be glycosylated in vivo. In the present specification all of the above illustrated modifications of the PAR1-receptor will be referred to as "functionally analogous peptides or proteins" in brief. Preferably PAR1 relates to SEQ ID NO:1.

In the context of the present invention the anti-PAR1 antibody may particularly be selected from the group of IgA-antibody, IgG-antibody and IgM-antibody, preferably an IgG antibody, e.g. IgG1, IgG2, IgG3 and IgG4.

Herein, the sample of the subject to be diagnosed in which the level of anti-PAR1 antibodies is to be determined is preferably a bodily fluid such as whole blood or lymph or fractions of blood such as serum or plasma. Preferably in the context of the present invention the sample is plasma or serum. The inventors found that antibody levels for anti-PAR1 antibodies are similar in serum samples and in plasma. However, in a preferred embodiment the sample in which the level of anti-PAR1 antibodies is to be detected is the same as the sample from which the control levels are derived. That is, if the levels are detected in a plasma sample of the subject to be diagnosed, the determined levels should be compared to control levels derived from plasma samples of the respective control subject. It is also clear from the results provided herewith, that the nature of the so chosen sample does not change the ratio of the levels in cancer patients when comparing them to the control levels measured in the same type of sample.

Where appropriate, the sample may need to be homogenized, or extracted with a solvent prior to use in the present invention in order to obtain a liquid sample. A liquid sample hereby may be a solution or suspension. Liquid samples may be subjected to one or more pre-treatments prior to use in the present invention. Such pre-treatments include, but are not limited to dilution, filtration, centrifugation, concentration, sedimentation, precipitation, dialysis. Pre-treatments may also include the addition of chemical or biochemical substances to the solution, such as acids, bases, buffers, salts, solvents, reactive dyes, detergents, emulsifiers, chelators.

"Plasma" in the context of the present invention is the virtually cell-free supernatant of blood containing anticoagulant obtained after centrifugation. Exemplary anticoagulants include calcium ion binding compounds such as EDTA or citrate and thrombin inhibitors such as heparinates or hirudin. Cell-free plasma can be obtained by centrifugation of the anticoagulated blood (e.g. citrated, EDTA or heparinized blood) for at least 15 minutes at 2000 to 3000 g.

"Serum" is the liquid fraction of whole blood that is collected after the blood is allowed to clot. When coagulated blood (clotted blood) is centrifuged serum can be obtained as supernatant. It does not contain fibrinogen, although some clotting factors remain.

In the method of the present invention, the anti-PAR1 antibody is preferably detected in an immunoassay. Suitable immunoassays may be selected from the group of immunoprecipitation, enzyme immunoassay (EIA)), enzyme-linked immunosorbenassys (ELISA), radioimmunoassay (RIA), fluorescent immunoassay, a chemiluminescent assay, an agglutination assay, nephelometric assay, turbidimetric assay, a Western Blot, a competitive immunoassay, a non-competitive immunoassay, a homogeneous immunoassay a heterogeneous immunoassay, a bioassay and a reporter assay such as a luciferase assay or FACS based assays like Luminex®. Preferably herein the immunoassay is an enzyme linked immunosorbent assay (ELISA).

The immunoassays can be homogenous or heterogeneous assays, competitive and non-competitive assays. In a particularly preferred embodiment, the assay is in the form of a sandwich assay, which is a non-competitive immunoassay, wherein the anti-PAR1 antibody (i.e. the "analyte") to be detected and/or quantified is allowed to bind to an immobilized PAR1 protein or immunogenic peptide fragment thereof and to a secondary antibody. The PAR1 or fragment thereof (i.e. a peptide), may e.g., be bound to a solid phase, e.g. a bead, a surface of a well or other container, a chip or a strip, and the secondary antibody is an antibody which is labeled, e.g. with a dye, with a radioisotope, or a reactive or catalytically active moiety such as a peroxidase, e.g. horseradish peroxidase. The amount of labeled antibody bound to the analyte is then measured by an appropriate method. The general composition and procedures involved with "sandwich assays" are well-established and known to the skilled person (*The Immunoassay Handbook*, Ed. David Wild, Elsevier LTD, Oxford; 3rd ed. (May 2005), *ISBN*-13: 978-0080445267; Hultschig C et al., *Curr Opin Chem Biol.* 2006 February; 10(1):4-10. PMID: 16376134, incorporated herein by reference). Sandwich immunoassays can for example be designed as one-step assays or as two-step assays.

The detectable label may for example be based on fluorescence or chemiluminescence. The labelling system comprises rare earth cryptates or rare earth chelates in combination with a fluorescence dye or chemiluminescence dye, in particular a dye of the cyanine type. In the context of the present invention, fluorescence based assays comprise the use of dyes, which may for instance be selected from the group comprising FAM (5-or 6-carboxyfluorescein), VIC, NED, Fluorescein, Fluoresceinisothiocyanate (FITC), IRD-700/800, Cyanine dyes, such as CY3, CY5, CY3.5, CY5.5, Cy7, Xanthen, 6-Carboxy-2',4',7',4,7-hexachlorofluorescein (HEX), TET, 6-Carboxy-4',5'-dichloro-2',7'-dimethodyfluorescein (JOE), N,N,N',N'-Tetramethyl-6-carboxyrhodamine (TAMRA), 6-Carboxy-X-rhodamine (ROX), 5-Carboxyrhodamine-6G (R6G5), 6-carboxyrhodamine-6G (RG6), Rhodamine, Rhodamine Green, Rhodamine Red, Rhodamine 110, BODIPY dyes, such as BODIPY TMR, Oregon Green, Coumarines such as Umbelliferone, Benzimides, such as Hoechst 33258; Phenanthridines, such as Texas Red, Yakima Yellow, Alexa Fluor, PET, Ethidiumbromide, Acridinium dyes, Carbazol dyes, Phenoxazine dyes, Porphyrine dyes, Polymethin dyes, and the like.

In the context of the present invention, chemiluminescence based assays comprise the use of dyes, based on the physical principles described for chemiluminescent materials in *Kirk-Othmer, Encyclopedia of chemical technology*, *4th ed.*, executive editor, J. L Kroschwitz; editor, M Howe-Grant, John Wiley & Sons, 1993, vol. 15, p. 518-562, incorporated herein by reference, including citations on pages 551-562. Preferred chemiluminescent dyes are acridiniumesters.

The "sensitivity" of an assay relates to the proportion of actual positives which are correctly identified as such, i.e. the ability to identify positive results (true positives positive results/number of positives). Hence, the lower the concentrations of the analyte that can be detected with an assay, the more sensitive the immunoassay is. The "specificity" of an assay relates to the proportion of negatives which are correctly identified as such, i.e. the ability to identify negative results (true negatives/negative results). For an antibody the "specificity" is defined as the ability of an individual antigen binding site to react with only one antigenic epitope. The binding behaviour of an antibody can also be characterized in terms of its "affinity" and its "avidity". The "affinity" of an antibody is a measure for the strength of the reaction between a single antigenic epitope and a single antigen binding site. The "avidity" of an antibody is a measure for the overall strength of binding between an antigen with many epitopes and multivalent antibodies.

An "immunogenic peptide" or "antigenic peptide" as used herein is a portion of a PAR1 protein that is recognized (i.e., specifically bound) by the anti-PAR1 antibody. Such immunogenic peptides generally comprise at least 5 amino acid residues, more preferably at least 10, and still more preferably at least 20 amino acid residues of PAR1. However, they may also comprise at least 30, 40, 50, 60, 70, 80, 90, 100, 110, 120, 130, 140 or 150 amino acid residues. For example, a PAR1 polypeptide fragment corresponding to an extracellular part of or comprising the extracellular part of PAR1, e.g. residues 42-102 of PAR1 (preferably as set out in SEQ ID NOs: 1 or 2) can be used in the context of the diagnostic methods and immunoassays of the present invention.

The antibodies to be detected or determined according to the present invention are directed against PAR1. This means that the antibodies specifically bind PAR1. Specific binding of an antibody normally occurs via binding of a binding site of the antigen, i.e. the epitope. The antibodies of the present invention are those specifically binding to PAR1. This binding may occur via recognition of sequence or structural epitopes. The skilled person is aware of methods of how to determine specific epitopes, e.g. fragments of the antigen PAR1, which are recognized and bound by the antibodies to be determined. Fragments of PAR1 binding to the auto antibodies are called immunogenic fragments. Methods for determining fragments of an antigen binding the antibody are described in several publications (e.g. Gershoni, J M; Roitburd-Berman, A; Siman-Tov, D D; Tarnovitski Freund, N; Weiss, Y (2007). "Epitope mapping: The first step in developing epitope-based vaccines". BioDrugs 21 (3): 145-56; Westwood, M R; Hay, F C (2001). Epitope Mapping: a practical approach. Oxford, Oxfordshire: Oxford University Press. ISBN 0-19-963652-4; Flanagan et al. (2011), "Mapping Epitopes with H/D-Ex Mass Spec". Genetic Engineering and Biotechnology news; 31(1); Gaseitsiwe, S.; Valentini, D.; Mandavifar, S.; Reilly, M.; Ehrnst, A.; Maeurer, M. (2009) "Peptide Microarray-Based Identification of Mycobacterium tuberculosis Epitope Binding to HLA-DRB1*0101, DRB1*1501, and DRB1*0401". Clinical and Vaccine Immunology 17 (1): 168-75; Linnebacher, Michael; Lorenz, Peter; Koy, Cornelia; Jahnke, Annika; Born, Nadine; Steinbeck, Felix; Wollbold, Johannes; Latzkow, Tobias et al. (2012). "Clonality characterization of natural epitope-specific antibodies against the tumor-related antigen topoisomerase IIa by peptide chip and proteome analysis: A pilot study with colorectal carcinoma patient samples" Analytical and Bioanalytical Chemistry 403 (1): 227-38; Cragg, M. S. (2011). "CD20 antibodies: Doing the time warp". Blood 118 (2): 219-20; Banik, Soma S. R.; Doranz, Benjamin J. (2010). "Mapping Complex Antibody Epitopes". Genetic Engineering and Biotechnology News 3 (2): 25-8; and Paes, Cheryl; Ingalls, Jada; Kampani, Karan; Sulli, Chidananda; Kakkar, Esha; Murray, Meredith; Kotelnikov, Valery; Greene, Tiffani A. et al. (2009). "Atomic-Level Mapping of Antibody Epitopes on a GPCR". Journal of the American Chemical Society 131 (20): 6952-4). In context with the present invention anti-PAR1 antibodies are understood as any immunoglobulin specifically recognizing/binding to PAR1, preferably PAR1 as set out above.

For the purposes of the immunoassays and diagnostic methods of the invention PAR1 by expression in cells, preferably eukaryotic cells or in cell free, preferably eukaryotic cell free systems. Hence, in the assays and methods of the invention PAR1 may be present in its natural cellular environment and can be used together with the material associated with the receptor in its natural state as well as in isolated form. Suitable expression systems include Chinese hamster ovary (CHO) cells overexpressing the human PAR1. Hence, cell extracts (particularly extracts from CHO cells overexpressing the human PAR1) can be used to detect anti-PAR1 antibodies. Based on the weight of the whole receptor in the preparation (e.g. the "extract") to be used according to the invention, the isolated receptor should account for at least 0.5%, preferably at least 5% more preferably at least 25%, and in a particular preferred embodiment at least 50%. The receptor is preferably used in isolated form, i.e. essentially free of other proteins, lipids, carbohydrates or other substances naturally associated with the receptor. "Essentially free of" means that the receptor is at least 75%, preferably at least 85%, more preferably at least 95% and especially preferably at least 99% free of other proteins, lipids, carbohydrates or other substances naturally associated with the receptor.

In particular, the method of the present invention comprises the steps of (a) contacting the sample with PAR1 or an antigenic peptide fragment under conditions allowing for the formation of a complex between anti-PAR1 antibodies with PAR1 or a peptide fragment thereof, (b) detecting the complex.

Hence, the invention relates to an immunoassay method for detecting a anti-PAR1 antibody in a sample from a subject, comprising the steps of (a) contacting the sample suspected of comprising an anti-PAR1 antibody with PAR1 or an antigenic peptide fragment thereof under conditions allowing for the formation of a complex between the anti-PAR1 antibody with PAR1 or the peptide fragment thereof, (b) detecting the complex.

The PAR1 or the peptide fragment thereof may preferably be immobilized on a surface. The complex may for example be detected using a secondary antibody against the Fc portion of the anti-PAR1 antibody. When the anti-PAR1 antibody is an IgG-antibody, the secondary antibody may be an anti-IgG antibody. In a particular embodiment, the subject is a human and (i) the anti-PAR1 antibody is a IgG1-antibody and the secondary antibody is an anti-human-IgG1 antibody; or (ii) the anti-PAR1 antibody is a IgG2-antibody and the secondary antibody is an anti-human-IgG2 antibody; or (iii) the anti-PAR1 antibody is a IgG3-antibody and the secondary antibody is an anti-human-IgG3 antibody; or (iv) the anti-PAR1 antibody is a IgG4-antibody and the secondary antibody is an anti-human-IgG4 antibody.

The secondary antibody may for example be labeled with a detectable marker, e.g. a peroxidase.

Furthermore, in the methods of the present invention further parameters of the subject may be considered as well. Such parameters in a multivariate model may include gender, age, histological evaluation, Figo staging or histopathological grading of the tumour and other markers. Dependent variables for determining survival may also be time till death, time till first relapse, time till death or first relapse (shorter interval if both events occurred). A Cox-Proportional-Hazard regression predicts the dependent variable based on one or more independent variables. These predictors can either be measures (as e.g. level of a biomarker) or categorical data (as e.g. response to a previous treatment). The skilled person is aware of the fact that diagnostic markers only give a certain degree of sensitivity and specificity, as also outlined herein. He knows that different further parameters might be considered in order to increase both. For example, when detecting levels of a marker indicative for epithelial cancer, inter alia ovarian cancer, the skilled person would not diagnose ovarian cancer in a male human subject. Nevertheless, the present invention provides a new and superior marker for diagnosis, prognosis of cancer, particularly for ovarian cancer. In the context of the methods of the invention and particularly the immunoassays of the invention, the presence of one or more further diagnostic markers for ovarian cancer is detected in the sample. For example, in a diagnostic method of the present invention levels of CA125, Human Epidymis Protein 4 (HE4) and/or Mesothelin are detected in addition.

The invention also relates to the use of PAR1 or an antigenic peptide fragment thereof for the diagnosis of a cancer, preferably selected from the group consisting of ovarian cancer, a solid organ cancer, squamous cell carcinoma, squamous cell carcinoma, metastatic cancer, preferably an epithelial cancer, preferably selected from the group consisting of ovarian cancer, breast cancer, renal cancer, colon cancer, colorectal cancer, and lung cancer, particularly preferred ovarian cancer.

In the context of the present invention, the levels of the anti-PAR1 antibodies a may be analyzed in a number of fashions well known to a person skilled in the art. For example, each assay result obtained may be compared to a "normal" value, or a value indicating a particular disease or outcome. A particular diagnosis/prognosis may depend upon the comparison of each assay result to such a value, which may be referred to as a diagnostic or prognostic "threshold". In certain embodiments, assays for one or more diagnostic or prognostic indicators are correlated to a condition or disease by merely the presence or absence of the indicator(s) in the assay. For example, an assay can be designed so that a positive signal only occurs above a particular threshold concentration of interest, and below which concentration the assay provides no signal above background.

The sensitivity and specificity of a diagnostic and/or prognostic test depends on more than just the analytical "quality" of the test, they also depend on the definition of what constitutes an abnormal result. In practice, Receiver Operating Characteristic curves (ROC curves), are typically calculated by plotting the value of a variable versus its relative frequency in "normal" (i.e. apparently healthy individuals not having ovarian cancer) and "disease" populations. For any particular marker, a distribution of marker levels for subjects with and without a disease will likely overlap. Under such conditions, a test does not absolutely distinguish normal from disease with 100% accuracy, and the area of overlap indicates where the test cannot distinguish normal from disease. A threshold is selected, below which the test is considered to be abnormal and above which the test is considered to be normal. The area under the ROC curve is a measure of the probability that the perceived measurement will allow correct identification of a condition. ROC curves can be used even when test results don't necessarily give an accurate number. As long as one can rank results, one can create a ROC curve. For example, results of a test on "disease" samples might be ranked according to degree (e.g. 1=low, 2=normal, and 3=high). This ranking can be correlated to results in the "normal" population, and a ROC curve created. These methods are well known in the art. See, e.g., Hanley et al. 1982. *Radiology* 143: 29-36. Preferably, a threshold is selected to provide a ROC curve area of greater than about 0.5, more preferably greater than about 0.7, still more preferably greater than about 0.8, even more preferably greater than about 0.85, and most preferably greater than about 0.9. The term "about" in this context refers to +/−5% of a given measurement.

The horizontal axis of the ROC curve represents (1-specificity), which increases with the rate of false positives. The vertical axis of the curve represents sensitivity, which increases with the rate of true positives. Thus, for a particular cut-off selected, the value of (1-specificity) may be determined, and a corresponding sensitivity may be obtained. The area under the ROC curve is a measure of the probability that the measured marker level will allow correct identification of a disease or condition. Thus, the area under the ROC curve can be used to determine the effectiveness of the test.

In other embodiments, a positive likelihood ratio, negative likelihood ratio, odds ratio, or hazard ratio is used as a measure of a test's ability to predict risk or diagnose a disease. In the case of a positive likelihood ratio, a value of 1 indicates that a positive result is equally likely among subjects in both the "diseased" and "control" groups; a value greater than 1 indicates that a positive result is more likely in the diseased group; and a value less than 1 indicates that a positive result is more likely in the control group. In the case of a negative likelihood ratio, a value of 1 indicates that a negative result is equally likely among subjects in both the "diseased" and "control" groups; a value greater than 1 indicates that a negative result is more likely in the test group; and a value less than 1 indicates that a negative result is more likely in the control group.

In the case of an odds ratio, a value of 1 indicates that a positive result is equally likely among subjects in both the "diseased" and "control" groups; a value greater than 1 indicates that a positive result is more likely in the diseased group; and a value less than 1 indicates that a positive result is more likely in the control group.

In the case of a hazard ratio, a value of 1 indicates that the relative risk of an endpoint (e.g., death) is equal in both the "diseased" and "control" groups; a value greater than 1 indicates that the risk is greater in the diseased group; and a value less than 1 indicates that the risk is greater in the control group.

The skilled artisan will understand that associating a diagnostic or prognostic indicator, with a diagnosis or with a prognostic risk of a future clinical outcome is a statistical analysis. For example, a marker level of lower than X may signal that a patient is more likely to suffer from an adverse outcome than patients with a level more than or equal to X, as determined by a level of statistical significance. Additionally, a change in marker concentration from baseline levels may be reflective of patient prognosis, and the degree of change in marker level may be related to the severity of adverse events. Statistical significance is often determined by comparing two or more populations, and determining a confidence interval and/or a p value. See, e.g., Dowdy and Wearden, *Statistics for Research*, John Wiley & Sons, New York, 1983. Preferred confidence intervals of the invention are 90%, 95%, 97.5%, 98%, 99%, 99.5%, 99.9% and 99.99%, while preferred p values are 0.1, 0.05, 0.025, 0.02, 0.01, 0.005, 0.001, and 0.0001.

Suitable threshold levels for the stratification of subjects into different groups (categories) have to be determined for each particular combination of PAR1-antibodies, disease and/or medication. This can e.g. be done by grouping a reference population of patients according to their level of PAR1-antibodies into certain quantiles, e.g. quartiles, quintiles or even according to suitable percentiles. For each of the quantiles or groups above and below certain percentiles, hazard ratios can be calculated comparing the risk for an adverse outcome, i.e. an "cancer" or a "non response", e.g. in terms of survival rate/mortality, between those patients who have received a certain medication and those who did not, or in terms of presence and absence of cancer in patients. In such a scenario, a hazard ratio (HR) above 1 indicates a higher risk for an adverse outcome for the patients who have received a treatment than for patients who did not. A HR below 1 indicates beneficial effects of a certain treatment in the group of patients. A HR around 1 (e.g. +/−0.1) indicates no elevated risk but also no benefit from medication for the particular group of patients. By comparison of the HR between certain quantiles of patients with each other and with the HR of the overall population of patients, it is possible to identify those quantiles of patients who have an elevated risk and those who benefit from medication and thereby stratify subjects according to the present invention.

In some cases presence of cancer, relapse and/or mortality upon treatment with an angiogenesis inhibitor will affect patients with high levels (e.g. in the fifth quintile) of PAR1-antibodies, while in other cases only patients with low levels of PAR1-antibodies will be affected (e.g. in the first quintile). However, with the above explanations, a skilled person is able to identify those groups of patients having cancer, those groups that do respond to a medication and those groups that do not respond to the medication.

Exemplarily, some combinations of hormones and medications are listed for several diseases in the appended examples. In another embodiment of the invention, the diagnosis, risk for relapse of cancer and/or mortality and/or outcome for a patient are determined by relating the patient's individual level of marker peptide to certain percentiles (e.g. 97.5th percentile) of a healthy population.

Kaplan-Meier estimators may be used for the assessment or prediction of the outcome or risk (e.g. diagnosis, relapse, progression or morbidity) of a patient.

The invention also pertains to a research and/or diagnostic kit for the diagnosis of ovarian cancer or for the prediction of risk stratification for relapse of ovarian cancer and/or mortality in a patient, wherein the kit comprises PAR1 or an antigenic peptide fragment thereof. The kit may further comprise an antibody directed to the Fc portion of the anti-PAR1 antibody to be detected, i.e. an anti-human IgG antibody.

Such kits can comprise a carrier, package or container that is compartmentalized to receive one or more containers such as vials, tubes, and the like, each of the container(s) comprising one of the separate elements to be used in the method. The kit of the invention will typically comprise the container described above and one or more other containers comprising materials desirable from a commercial and user standpoint, including buffers, diluents, filters, needles, syringes, and package inserts with instructions for use. In addition, a label can be provided on the container to indicate that the composition is used for a specific therapeutic or non-therapeutic application, and can also indicate directions for either in vivo or in vitro use, such as those described herein. Directions and or other information can also be included on an insert which is included with the kit.

The term "drug" in connection with the present invention is to be understood as any substance, pharmaceutical composition or the like which are intended for the treatment of cancer, preferably an epithelial cancer as outlined herein, particularly preferred ovarian cancer. Different drugs are known. In a preferred embodiment the drug used for the treatment of cancer are drugs directed against angiogenesis, i.e. angiogenesis inhibitors. Angiogenesis is a physiological process through which new blood vessels form from pre-existing vessels and plays a fundamental role in the transition of tumors from a benign state to a malignant one. Angiogenesis inhibitors are therefore well known drugs for the treatment of cancer and are preferred in the present invention. They include and are preferably selected from the group consisting of bevacizumab and aflibercept. Bevacizumab (Trade name Avastin®, Roche) is a particularly preferred drug according to the present invention and is slows the growth of new blood vessels. It is licensed to treat various cancers, including colorectal cancer, lung cancer, breast cancer, glioblastoma, kidney (renal) renal and ovarian cancer. In a preferred embodiment the angiogenesis inhibitor is bevacizumab. Furthermore, the invention recites inhibitors of EGFR activity as a preferred drug. Such inhibitor is to be understood as every substance, molecule or composition which inhibits activity/activation of EGFR. The skilled person knows how EGFR is activated and how to determine whether a substance is able to inhibit EGFR activity. The epidermal growth factor receptor (EGFR) is a member of the ErbB family of receptors, a subfamily of four closely related receptor tyrosine kinases: EGFR (ErbB-1), HER2/c-neu (ErbB-2), Her 3 (ErbB-3) and Her 4 (ErbB-4). Mutations affecting EGFR expression or activity could result in cancer (Zhang H, Berezov A, Wang Q, Zhang G, Drebin J, Murali R, Greene MI (August 2007). "ErbB receptors: from oncogenes to targeted cancer therapies". J. Clin. Invest. 117 (8): 2051-8).

EGFR (epidermal growth factor receptor) exists on the cell surface and is activated by binding of its specific ligands, including epidermal growth factor and transforming growth factor α (TGFα). ErbB2 has no known direct activating ligand, and may be in an activated state constitutively or become active upon heterodimerization with other family members such as EGFR. Upon activation by its growth factor ligands, EGFR undergoes a transition from an inactive monomeric form to an active homodimer (Yosef Yarden and Joseph Schlessinger (1987). "Epidermal Growth-Factor Induces Rapid, Reversible Aggregation of the Purified Epidermal Growth-Factor Receptor". Biochemistry 26 (5): 1443-1451). In addition to forming homodimers after ligand binding, EGFR may pair with another member of the ErbB receptor family, such as ErbB2/Her2/neu, to create an activated heterodimer. Formation of clusters of activated EGFRs have been reported, although it remains unclear whether this clustering is important for activation itself or if it is a secondary effect occurring after activation by dimerization.

EGFR dimerization stimulates its intrinsic intracellular protein-tyrosine kinase activity and autophosphorylation of tyrosine (Y) residues in the C-terminal domain of EGFR occurs, e.g. Y992, Y1045, Y1068, Y1148 and Y1173 (Downward J, Parker P, Waterfield M D (1984). "Autophosphorylation sites on the epidermal growth factor receptor". Nature 311 (5985): 483-5). Thereby downstream activation and signaling is activated by binding of other proteins to the phosphorylated tyrosines through their phosphotyrosine-binding SH2 domains. These downstream signaling proteins initiate several signal transduction cascades, principally the MAPK, Akt and JNK pathways, leading to DNA synthesis and cell proliferation (Oda K, Matsuoka Y, Funahashi A, Kitano H (2005). "A comprehensive pathway map of epidermal growth factor receptor signaling". Mol. Syst. Biol. 1 (1): 2005.0010). Such proteins modulate phenotypes such as cell migration, adhesion, and proliferation. Activation of the receptor is important for the innate immune response in human skin. The kinase domain of EGFR can also cross-phosphorylate tyrosine residues of other receptors it is aggregated with, and can itself be activated in that manner.

The identification of EGFR as an oncogene has led to the development of anticancer therapeutics directed against EGFR, including gefitinib (Paez J G, Jänne P A, Lee J C, Tracy S, Greulich H, Gabriel S, Herman P, Kaye F J, Lindeman N, Boggon T J, Naoki K, Sasaki H, Fujii Y, Eck M J, Sellers W R, Johnson B E, Meyerson M' (June 2004). "EGFR mutations in lung cancer: correlation with clinical response to gefitinib therapy". Science 304 (5676): 1497-500), erlotinib, and cetuximab. Most of the therapeutic approaches target the misregulation of EGFR, i.e. inhibit EGFR activation. Cetuximab and panitumumab are examples of monoclonal antibody inhibitors used for treatment. Other monoclonal antibodies in clinical development are zalutumumab, nimotuzumab, and matuzumab. The monoclonal antibodies block the extracellular ligand binding domain. With the binding site blocked, signal molecules can no longer attach there and activate the tyrosine kinase.

Another method is using small molecules to inhibit the EGFR tyrosine kinase domain at the intracellular part. Without kinase activity, EGFR is unable to activate itself, which is a prerequisite for binding of downstream adaptor proteins. Ostensibly by halting the signaling cascade in cells that rely on this pathway for growth, tumor proliferation and migration is diminished. Gefitinib, erlotinib, and lapatinib (mixed EGFR and ERBB2 inhibitor) are examples of small molecule kinase inhibitors. There are several quantitative methods available that use protein phosphorylation detection to identify EGFR family inhibitors (Olive D M (October 2004). "Quantitative methods for the analysis of protein phosphorylation in drug development". Expert Rev Proteomics 1 (3): 327-41). New drugs such as gefitinib and erlotinib directly target the EGFR. Patients have been divided into EGFR-positive and EGFR-negative, based upon whether a tissue test shows a mutation. EGFR-positive patients have shown a 60% response rate, which exceeds the response rate for conventional chemotherapy. However, clear prediction of the response of a patient to a treatment is still an issue (Jackman D M, Miller V A, Cioffredi L A, Yeap B Y, Janne P A, Riely G J, Ruiz M G, Giaccone G, Sequist L V, Johnson B E (August 2009). "Impact of epidermal growth factor receptor and KRAS mutations on clinical outcomes in previously untreated non-small cell lung cancer patients: results of an online tumor registry of clinical trials". Clin. Cancer Res. 15 (16): 5267-73). Many patients develop resistance increasing the risk for relapse of cancer after treatment. Two primary sources of resistance are the T790M Mutation and MET oncogenes (Jackman et al (2009)). However, as of 2010 there was no consensus of an accepted approach to combat resistance nor FDA approval of a specific combination. Preclinical results have been reported for AP26113 which targets the T790M mutation.

Hence, in a preferred embodiment the EGFR inhibitor is selected from the group consisting of bevacizumab, panitumumab, traszuzumab, cetuximab, gfitinib, erlotinib, lapatinib, and vandetanib.

Also encompassed by the invention is a method of treating cancer, preferably ovarian cancer, in a subject, comprising determining the level of antibodies against PAR1 in a sample from the subject, wherein when the level of anti-PAR1 antibodies in a sample from the subject is above a level determined as the PAR1 antibody level in subjects showing no-response to said treatment, treatment is applied to the subject. Such a treatment comprises in a preferred embodiment the administration of a drug and may further, e.g., comprise surgery, and radiation therapy. Preferably the administration of a drug according to the said above is performed after surgery. Drugs used in the treatment of ovarian cancer include angiogenesis inhibitors or inhibitors of EGFR activity, such as therapeutic antibodies, e.g. bevacizumab (sold as Avastin® by Roche), or panitumumab.

The invention, thus, also relates to an angiogenesis inhibitor for use in the treatment of cancer in a subject, wherein the angiogenesis inhibitor is administered to the subject when a level of anti-PAR1 antibodies in a sample from the subject above a level determined as the control level for non-response to the treatment is determined, preferably using a method according to the present invention. The skilled person will acknowledge that the embodiments of the method for predicting whether a subject to be treated for cancer with a drug will respond to said treatment as outlined herein, also apply to the drug for use in the treatment. He will acknowledge that the drug is for use in the treatment of cancer in a subject, wherein the subject is predicted to respond to the treatment, i.e. if the PAR1 levels determined in the subject to be treated, e.g. using the method according to the present invention, are indicative for the response of the subject to the treatment. The cancer to be treated may be any cancer treated with angiogenesis inhibitors. The cancer to be treated may be selected from the group consisting of ovarian cancer, a solid organ cancer, squamous cell carcinoma, squamous cell carcinoma, metastatic cancer, preferably an epithelial cancer, preferably selected from the group consisting of ovarian cancer, breast cancer, renal cancer, colon cancer, colorectal cancer, and lung cancer, particularly preferred ovarian cancer. In one embodiment the invention also relates to an angiogenesis inhibitor for use in the treatment of cancer, preferably ovarian cancer, in a subject, wherein said angiogenesis inhibitor is administered to the subject when the level anti-PAR1 antibodies in a sample from the subject is above 0.6 units/ml, preferably when the level of anti-PAR1 antibodies in a sample is above 0.7 units/ml, preferably above 0.8 units/ml, more preferably above 0.9 units/ml. The angiogenesis inhibitor is preferably bevacizumab. Again, ratios may be applied. In such embodiment the angiogenesis inhibitor is preferably applied to the subject to be treated when the ratios are indicative for the response of the subject to said treatment with an angiogenesis inhibitor.

The invention, thus, also relates to an inhibitor of EGFR activity for use in the treatment of ovarian cancer in a subject, wherein said inhibitor of EGFR activity is administered to the subject when the level of anti-PAR1 antibodies in a sample from the subject is above 1.5 units/ml said inhibitor of EGFR activity is administered to the subject, preferably when the level of anti-PAR1 antibodies in a sample is above 1.7 units/ml, preferably above 2.0 units/ml, more preferably above 2.5 units/ml. The inhibitor of EGFR activity is preferably panitumumab. Again, ratios may be applied. In such embodiment the inhibitor of EGFR activity is preferably applied to the subject to be treated when the ratios are indicative for the response of the subject to said treatment with an inhibitor of EGFR activity.

The invention furthermore relates to a kit for diagnosing cancer as outlined above, or predicting the response of a cancer patient to the treatment for cancer, said kit comprising PAR1 or an antigenic peptide thereof, and means to detect antibodies binding to said PAR1 or peptide thereof. Preferably the kit is designed for a method of the present invention. It will be understood that the embodiments disclosed herein above for PAR1 or an antigenic peptide thereof as set out herein above also apply to the kit. The kit is designed to detect autoimmune antibodies in samples of subject and hence comprises means to detect such antibodies, particularly antibodies binding to said PAR1 or peptide thereof. Such means are outlined herein above, e.g. for immunoassays. The embodiments set out for the immunoassays apply also to the kit of the invention. The kits of the present invention are meant for the detection of autoimmune antibodies. Hence, in one embodiment they comprise means for the preparation of blood, e.g. for gaining serum thereof. Furthermore, the kit may comprise control composition and/or standards. The control composition preferably comprises PAR1 antibodies as positive control. Furthermore, the kit may comprise one or a plurality of standard compositions. A standard composition comprises PAR1 antibodies at a defined concentration. As outlined herein, determination of concentration of autoimmune-antibodies may be performed using standard curves. These curves set out which concentration of antibodies in a sample or solution corresponds to what read-out value of the assay used, e.g. optical density or proportion of optical density at different wavelengths (e.g. 450 nm/620 nm). To this end the kits of the present invention may comprise one or more standard compositions having a defined concentration of PAR1 antibodies, preferably of the kind to be detected in the method. A standard composition of the kits according to the present invention comprise PAR1 antibodies at concentrations selected from the group consisting of 40 Units/ml, 20 Units/ml, 10 Units/ml, 5 Units/ml and 2.5 Units/ml. In one embodiment the kit comprises five standard compositions with the recited concentration. In another embodiment the kit comprises one standard composition with the highest concentration of the standard curve, e.g. 40 units/ml or 20 units/ml. The other concentrations may be produced at the side of the end user by further dilutions, e.g. in PBS. A dilution buffer may therefore also be comprised in the kits according to the invention.

It will be readily understood that the embodiments outlined above shall apply to the invention as a whole and not be limited to a specific method, unless stated otherwise. It will for example be understood the embodiments for the type of cancer shall be applied to every method, kit or the like disclosed herein. The invention is further illustrated by the following non-limiting examples and figures.

Sequences

```
SEQ ID NO: 1:
Amino acid sequence of the human PAR1 receptor (isoform 1)
[SEQ ID NO: 1]:
    1 MGPRRLLLVA ACFSLCGPLL SARTPARRPE SKATNATLDP RSFLLRNPND
   51 KYEPFWEDEE KNESGLTEYR LVSINKSSPL QKQLPAFISE DASGYLTSSW
  101 LTLFVPSVYT GVFVVSLPLN IMAIVVFILK MNVKKPAVVY MLHLATADVL
  151 FVSVLPFKIS YYFSGSDWQF GSELCRFVTA AFYCNMYASI LLMTVISIDR
  201 FLAVVYPMQS LSWRTLGRAS FTCLAIWALA IAGVVPLLLK EQTIQVPGLN
  251 ITTCHDVLNE TLLEGYYAYY FSAFSAVFFF VPLIISTVCY VSIIRCLSSS
  301 AVANRSKKSR ALFLSAAVFC IFIICFGPTN VLLIVHYSFL SHTSTTEAAY
  351 FAYLLCVCVS SISCCIDPLI YYYASSECQR YVYSILCCKE SSDPSSYNSS
  401 GQLMASKMDT CSSNLNNSIY KKLLT SEQ ID NO: 2:
Amino acid sequence of the human PAR1 receptor (isoform 2)
[SEQ ID NO: 2]:
    1 MGPRRILIVA ACFSLCGPLL SARTRARRPE SKATNATLDP RSFLLRNPND
   51 KYEPFWEDEE KNESGLTEYR LVSINKSSPL QKQLPAFISE DASGYLTSSW
  101 LTLFVPSVYT GVFVVSLPLN IMAIVVFILK MNVKKPAVVY MLHLATADVL
  151 FVSVLPFKIS YYFSGSDWQF GSELCRFVTA AFYCNMYASI LLMTVISIDR
  201 FLAVVYPMQS LSWRTLGRAS FTCLAIWALA IAGVVPLLLK EQTIQVPGLN
  251 ITTCHDVLNE TLLEGYYAYY FSAFSAVFFF VPLIISTVCY VSIIRCLSSS
  301 AVANRSKKSR ALFLSAAVFC IFIICFGPTN VLLIAHYSFL SHTSTTEAAY
  351 FAYLLCVCVS SISCCIDPLI YYYASSECQR YVYSILCCKE SSDPSSYNSS
  401 GQLMASKMDT CSSNLNNSIY KKLLT
```

EXAMPLES

Example 1

We measured the anti-PAR1 autoantibody in serum samples using a sandwich ELISA kit (CellTrend GmbH Luckenwalde, Germany). The microtiter 96-well polystyrene plates were coated with chemically synthesized human PAR1 isoform 1 (SEQ ID NO:1). To maintain the conformational epitopes of the receptor, 1 mM calcium chloride was added to every buffer. Duplicate samples of a 1:100 serum dilution were incubated at 4° C. for 2 hours. After washing steps, plates were incubated for 60 minutes with a 1:20.000 dilution of horseradish-peroxidase-labeled goat anti-human IgG (Jackson, USA) used for detection. In order to obtain a standard curve, plates were incubated with test sera from an anti-PAR1 autoantibody positive index patient. The ELISA was validated according to the FDA's "Guidance for industry: Bioanalytical method validation".

To set a standard for the concentrations of the autoimmune antibodies, a standard curve was generated. In detail, a serum sample of a systemic sclerosis patient was diluted (a) 1:100 for standard point 40 Units/ml, (b) 1:200 for standard point 20 Units/ml, (c) 1:400 for standard point 10 Units/ml, (d) 1:800 for standard point 5 Units/ml and (e) 1:1600 for standard point 2.5 Units/ml. Then the optical density was determined using the kit and method of example 1. Each standard point was performed in duplicates.

Example 2

Anti-PAR1 antibody levels in serum samples from 132 healthy donors ("control") and 201 patients with ovarian cancer ("OvCA") were measured using the kit and method of example 1. The levels were determined in units/mL. FIG. 1 shows the mean values of the natural logarithm of the PAR1 antibody level for case and control subjects. Patient suffering from ovarian cancer had significantly lower levels (p<0.0001) of anti-PAR1 antibodies as compared to healthy controls.

Example 3

Figure 2:
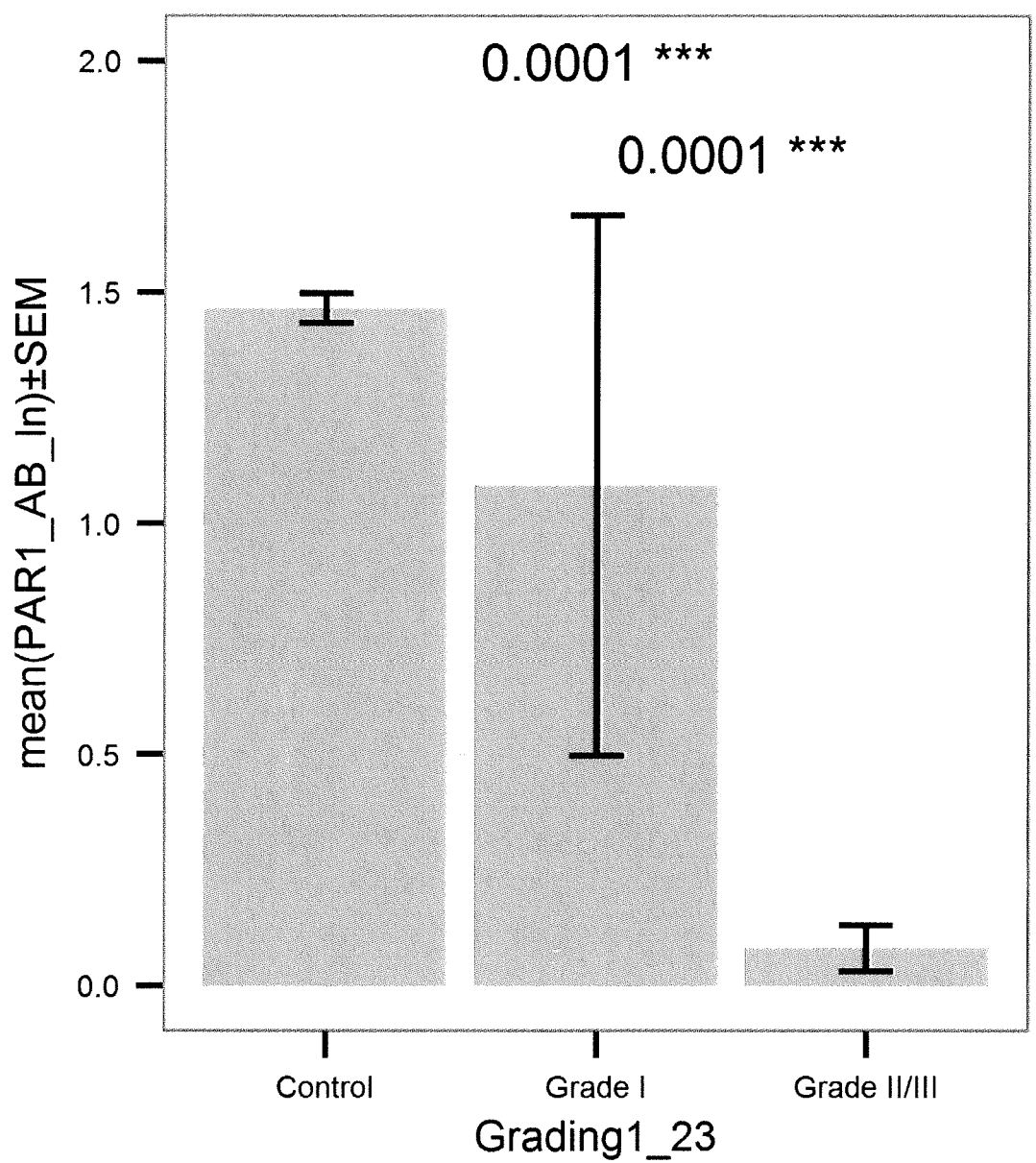
FIG. 2: Comparison of the mean level of anti-PAR1 antibodies (ln of units/ml) in serum samples of ovarian cancer patients suffering from histological Grade I ovarian cancer ("Grade I"; mean ln of units/ml=1.082; n=6) to the mean level of anti-PAR1 antibodies in serum samples of a ovarian cancer patients suffering from histological Grade II ovarian cancer ("Grade II/III", mean ln of units/ml=0.081 units/ml, n=192) and healthy control subjects ("Control", mean ln of units/ml=1.466 units/ml; n=132). The p-value is indicated on top. Bars indicate standard error of mean.

Anti-PAR1 antibody levels in serum samples from 132 healthy donors ("control"; see Example 1), 6 patients with ovarian cancer of histological (differentiation) Grade I ("Grade I") and 192 patients with proven ovarian cancer of histological (differentiation) Grade II or III ("Grade II/III") were measured using the kit and method of example 1. The levels were determined in units/mL. FIG. 2 shows the mean values of the natural logarithm of the PAR1 antibody level for case and control subjects. Patient suffering from ovarian cancer of Grade II or III had significantly lower levels (p<0.0001) of anti-PAR1 antibodies as compared to patients suffering from ovarian cancer of Grade I or healthy controls, respectively.

Example 4

Figure 3:
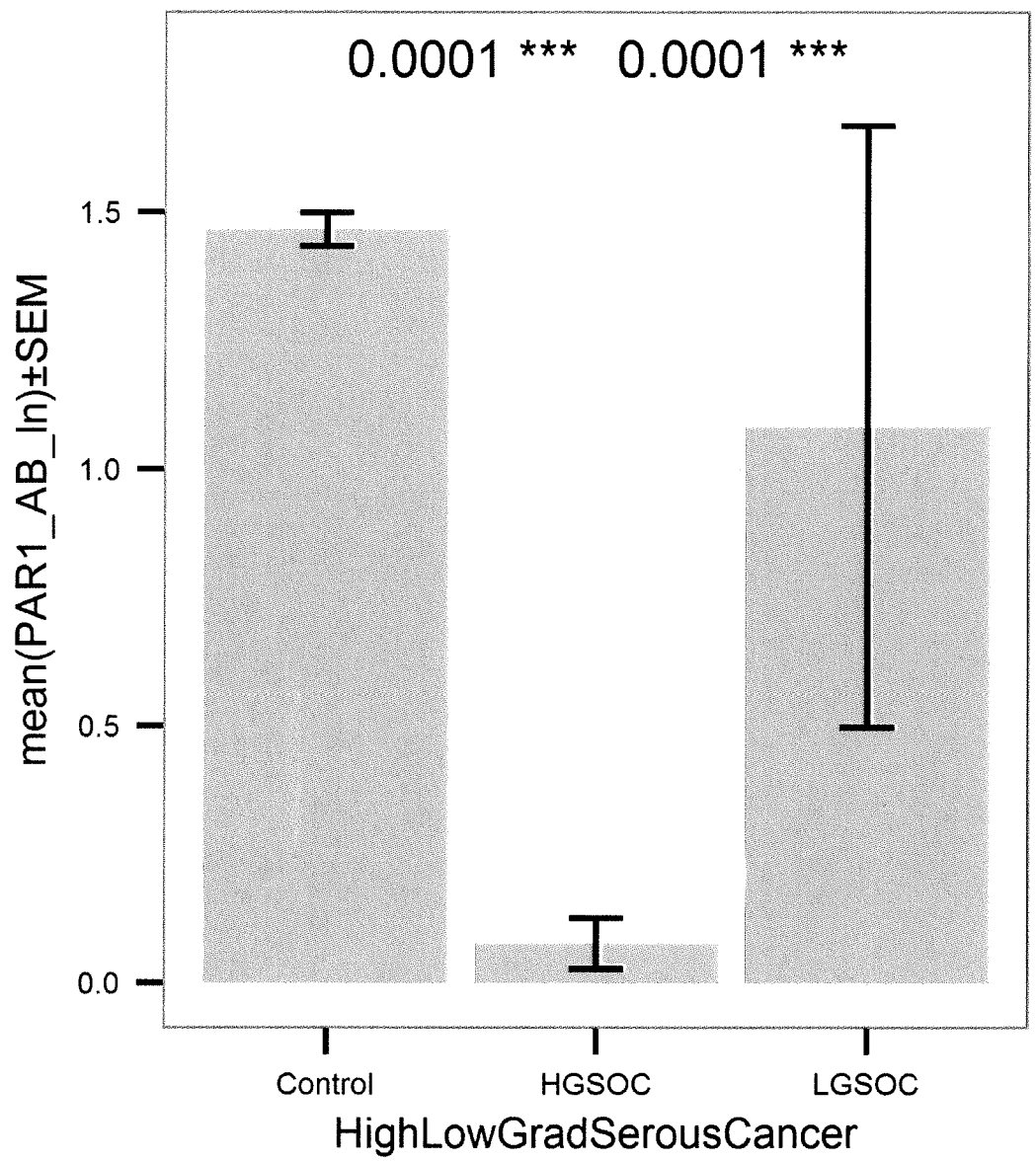
FIG. 3: Comparison of the mean level of anti-PAR1 antibodies (ln of units/ml) in serum samples of ovarian cancer patients suffering from Low Grade Serous Ovarian Cancer ("LGSOC"; mean ln of units/ml=1.082; n=6) to the median level of anti-PAR1 antibodies in serum samples of a ovarian cancer patients suffering from High Grade Serous Ovarian Cancer ("HGSOC", mean ln of units/ml=0.076 units/ml, n=184) and healthy control subjects ("Control", mean ln of units/ml=1.466 units/ml; n=132). The p-value is indicated on top. Bars indicate standard error of mean.

Anti-PAR1 antibody levels in serum samples from 132 healthy donors ("control"; see Example 1), 184 patients with High Grade Serous Ovarian Cancer ("HGSOC") and 6 patients with Low Grade Serous Ovarian Cancer ("LGSOC") were measured using the kit and method of example 1. The levels were determined in units/mL. FIG. 3 shows the mean values of the natural logarithm of the PAR1 antibody level for case and control subjects. Patient suffering from ovarian cancer of HGSOC had significantly lower levels (p<0.0001) of anti-PAR1 antibodies as compared to patients suffering from LGSOC or healthy controls, respectively.

Example 5

Figure 4:
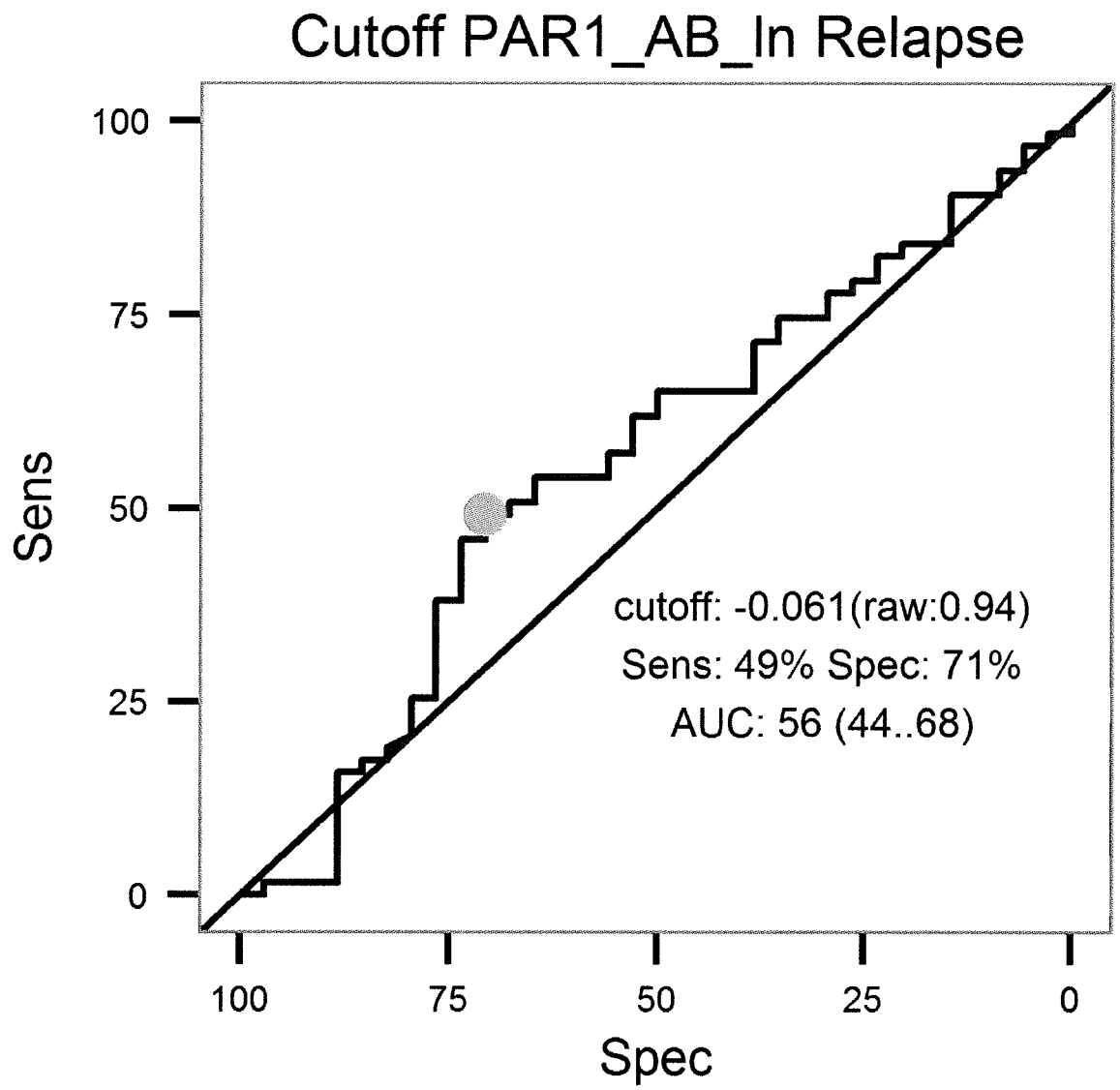
FIG. 4: A: On top sensitivity of the prediction of relapse of ovarian cancer after surgical removal of the tumor and subsequent chemotherapy with cisplatin or carboplatin is plotted against the specificity. Cutoff value On of units/ml=−0.061) and AUC is given in the graph. Below Kaplan-Meier estimators with the proportion of patients not showing relapse after surgical removal of the tumor and subsequent chemotherapy with cisplatin or carboplatin is shown over the time for patients having antibody levels below the ROC-cutoff value (dotted line) and above the ROC-cutoff value (solid line). B: On top sensitivity of the prediction of survival after surgical removal of the tumor and subsequent chemotherapy with cisplatin or carboplatin is plotted against the specificity. Cutoff value On of units/ml=−0.42) and AUC is given in the graph. Below Kaplan-Meier estimators with the proportion of patients surviving after surgical removal of the tumor and subsequent chemotherapy with cisplatin or carboplatin is shown over the time for patients having antibody levels below the ROC-cutoff value (dotted line) and above the ROC-cutoff value (solid line). C: on the left sensitivity of the prediction of a combined endpoint (death or relapse of cancer) of ovarian cancer patients after surgical removal of the tumor and subsequent chemotherapy with cisplatin or carboplatin is plotted against the specificity. Cutoff value On of units/ml=−0.85) and AUC is given in the graph. Below Kaplan-Meier estimators with the proportion of patients surviving or not showing relapse of cancer after surgical removal of the tumor and subsequent chemotherapy with cisplatin or carboplatin is shown over the time for patients having antibody levels below the ROC-cutoff value (dotted line) and above the ROC-cutoff value (solid line). D: comparison of the mean level of anti-PAR1 antibodies (units/ml) in serum samples of patients treated who died after chemotherapie and those who survived. Patients who died after chemotherpeutic treatment show higher values than patients who survived. Bars indicate error of mean.
Figure 4:
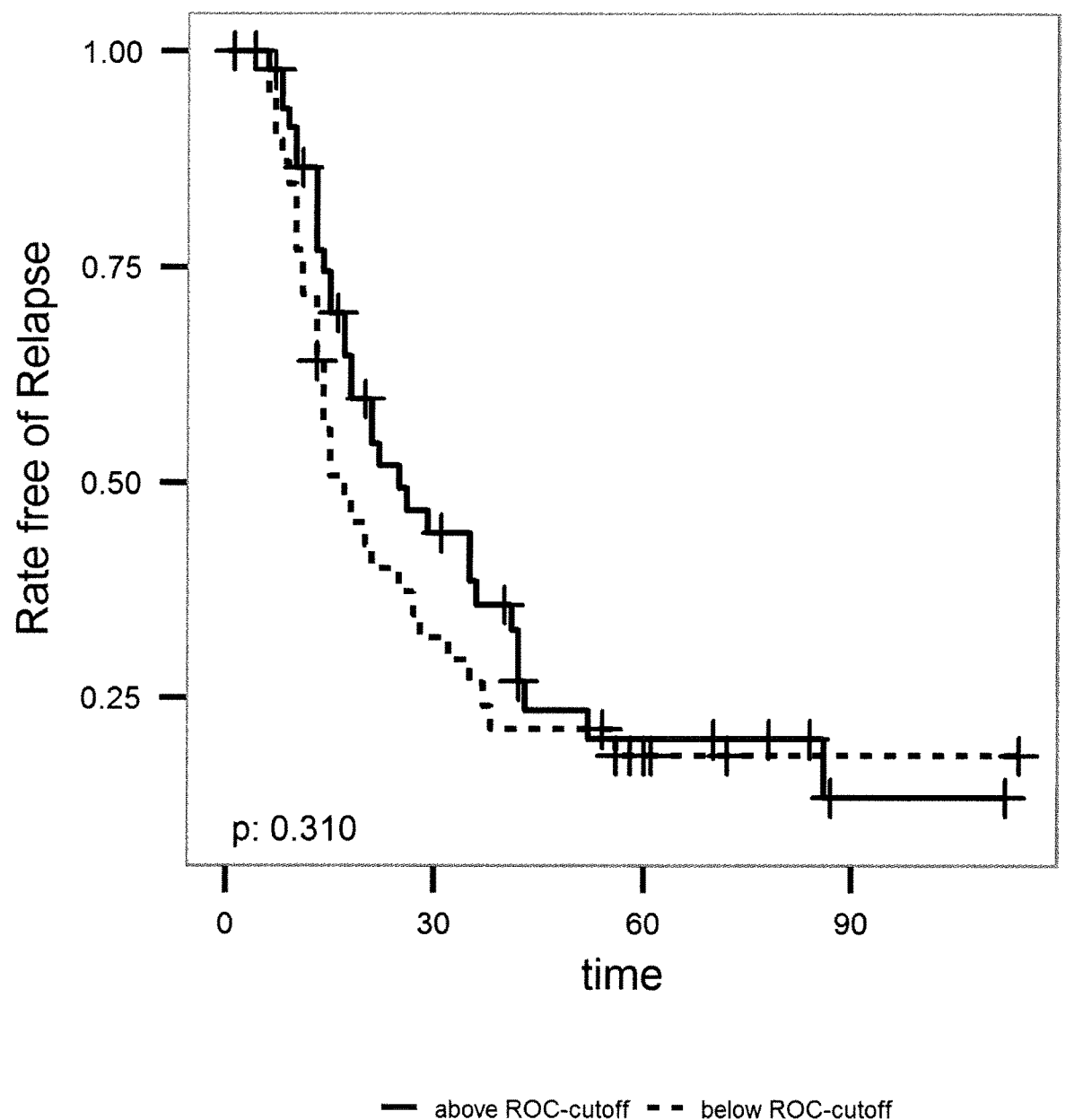
Figure 4:
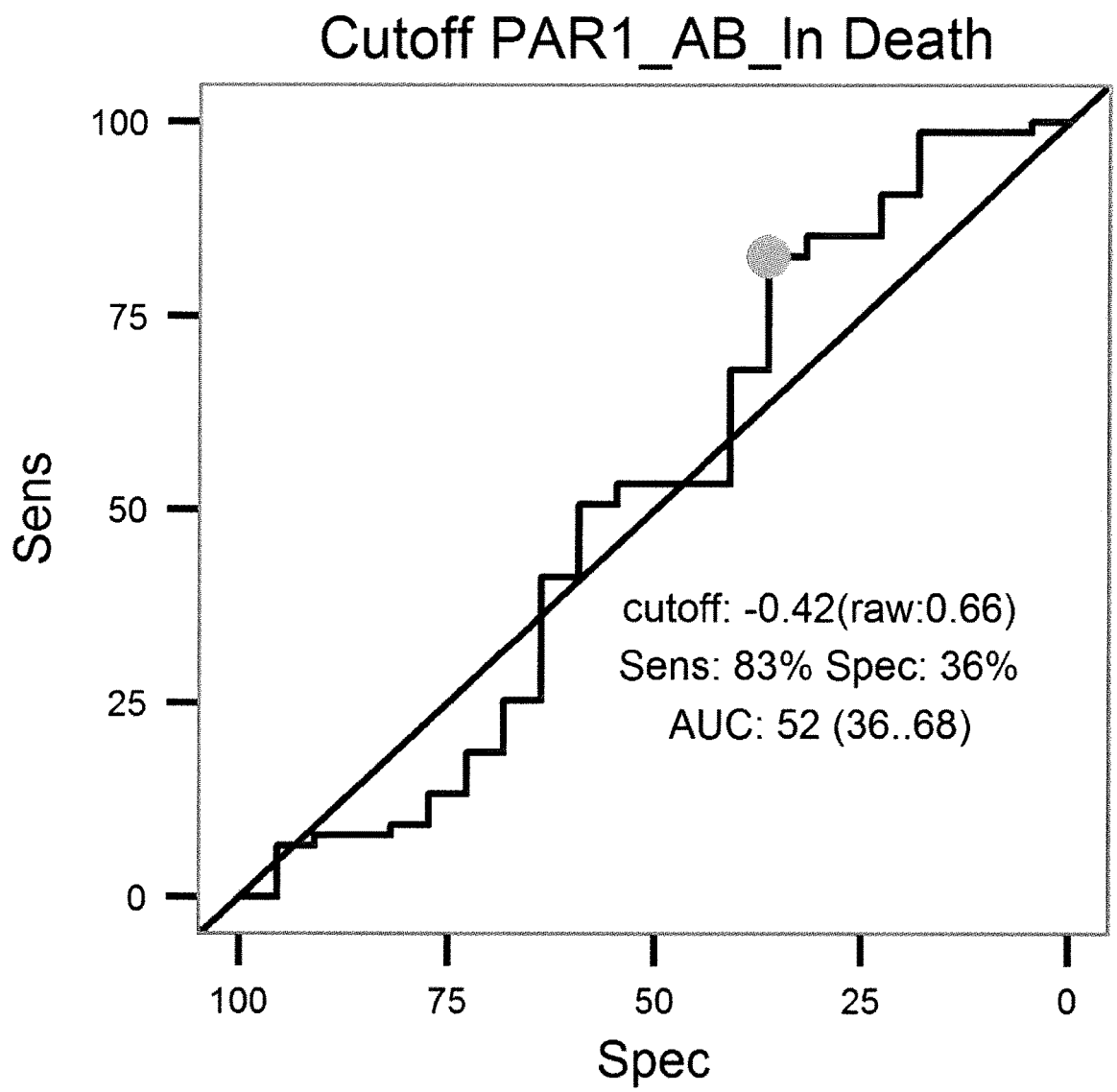
Figure 4:
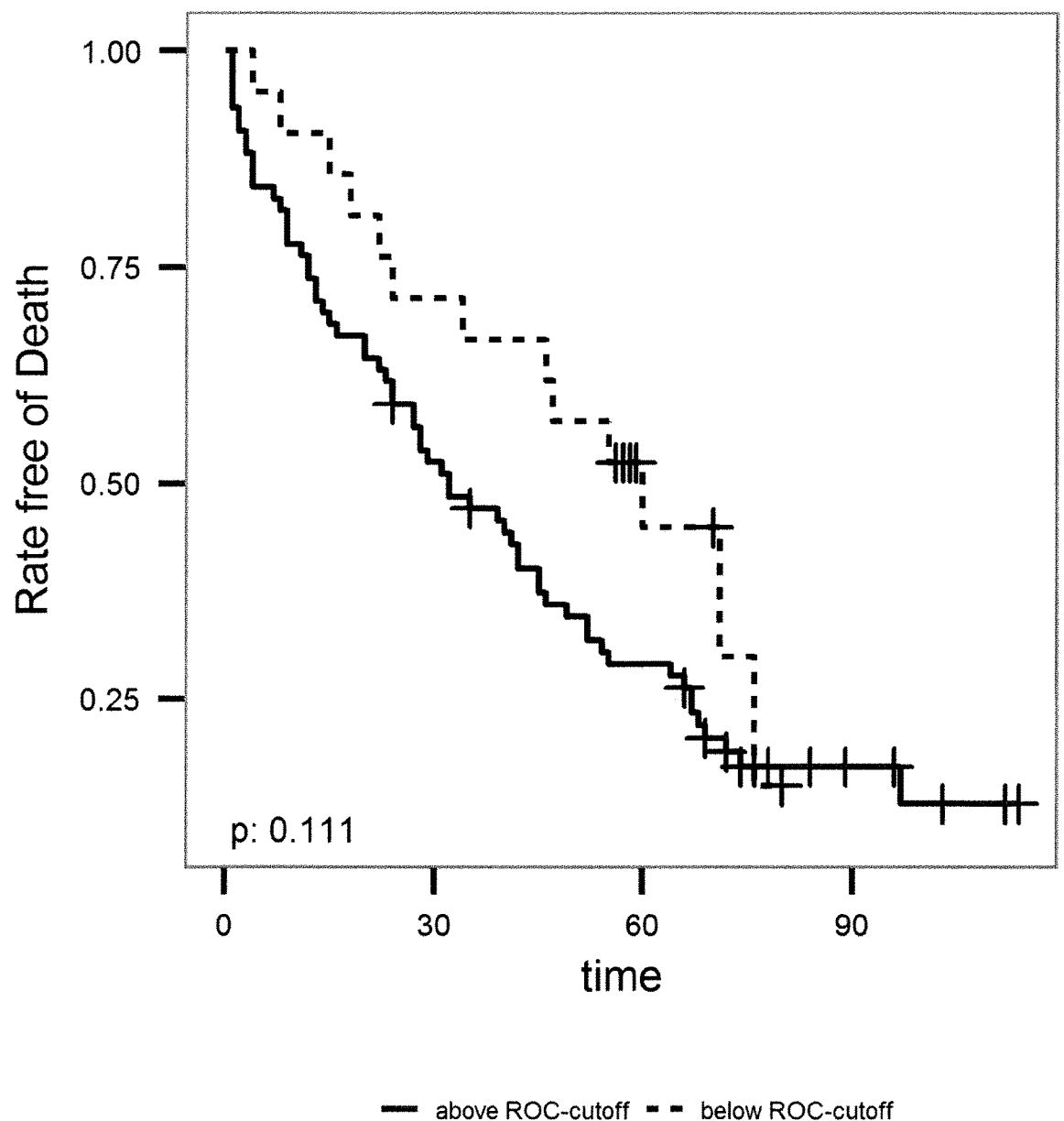
Figure 4:
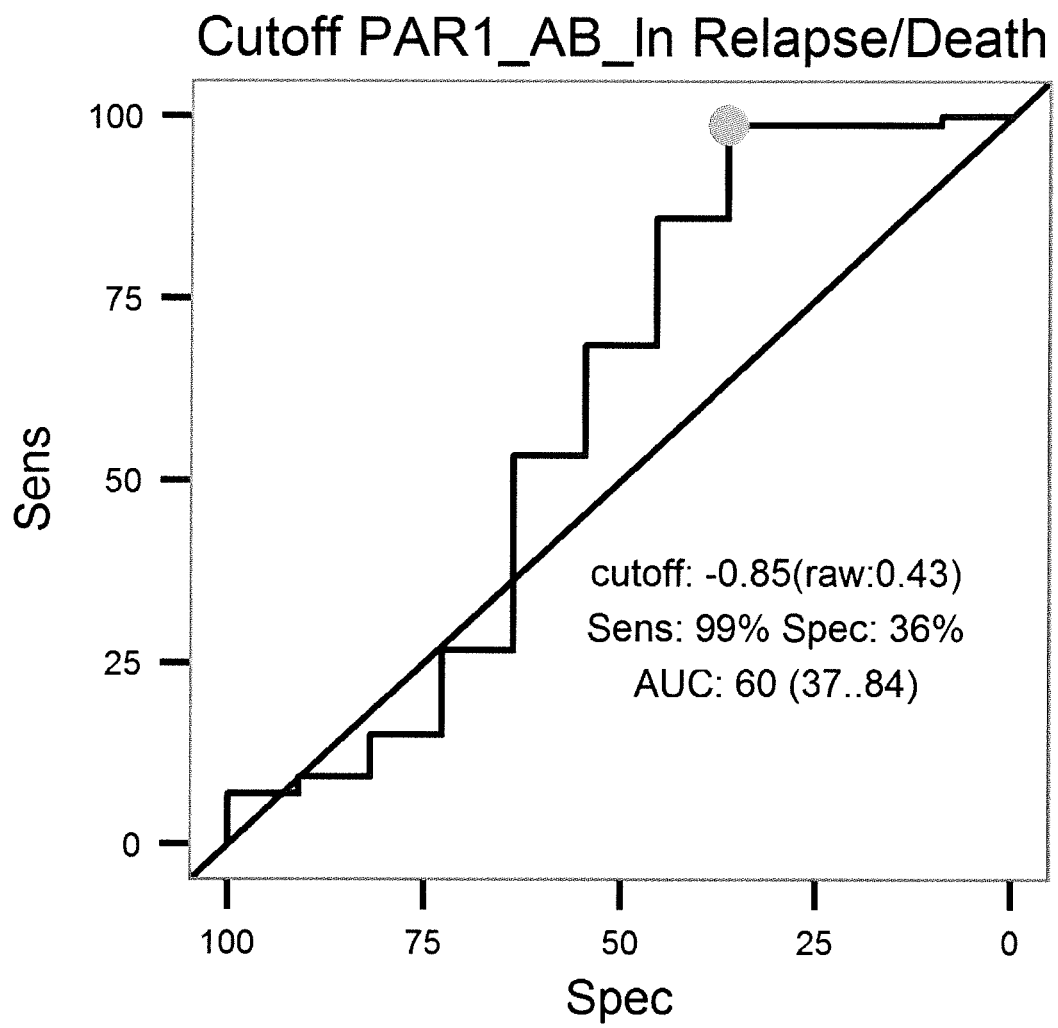
Figure 4:
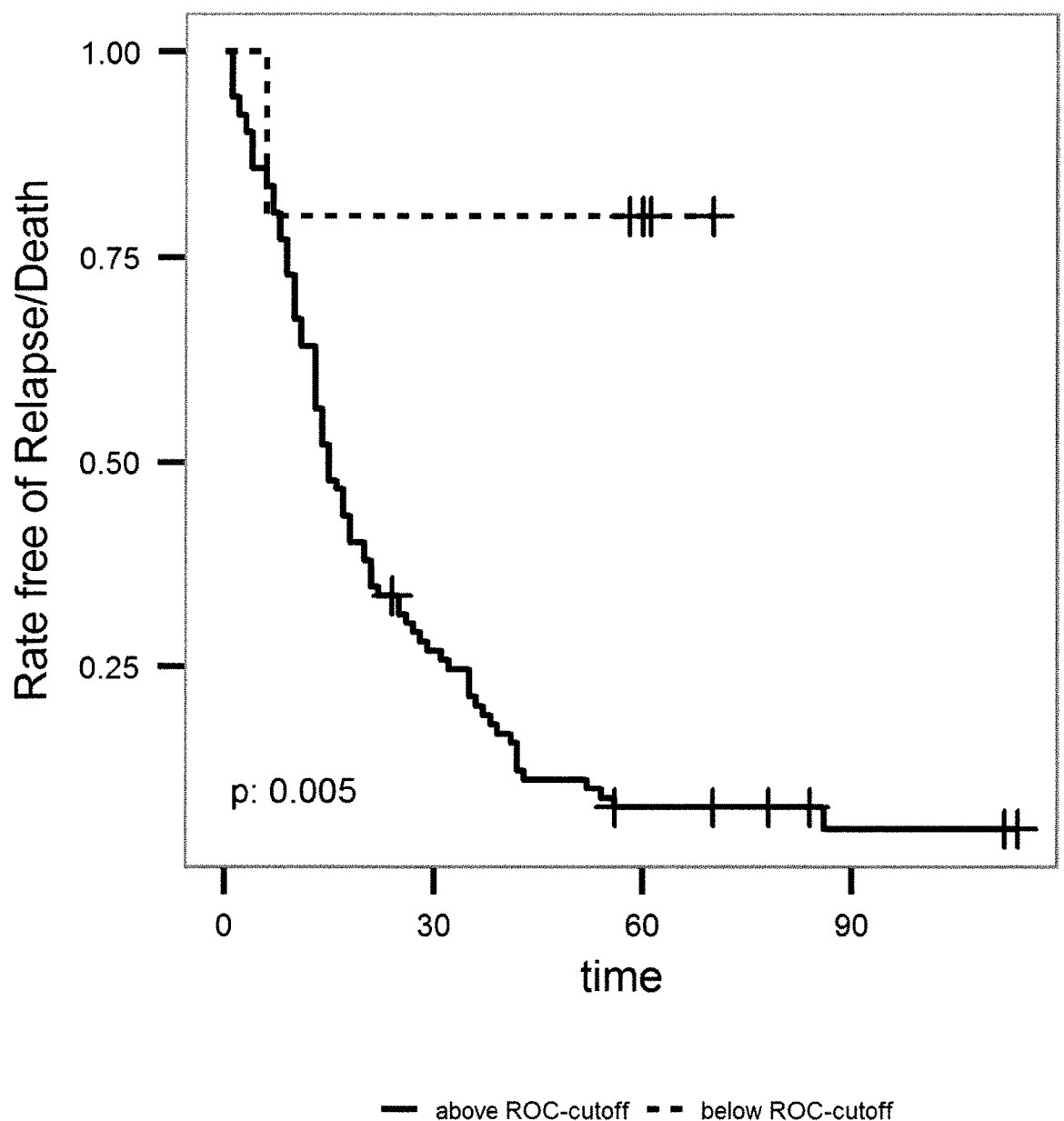
Figure 4:
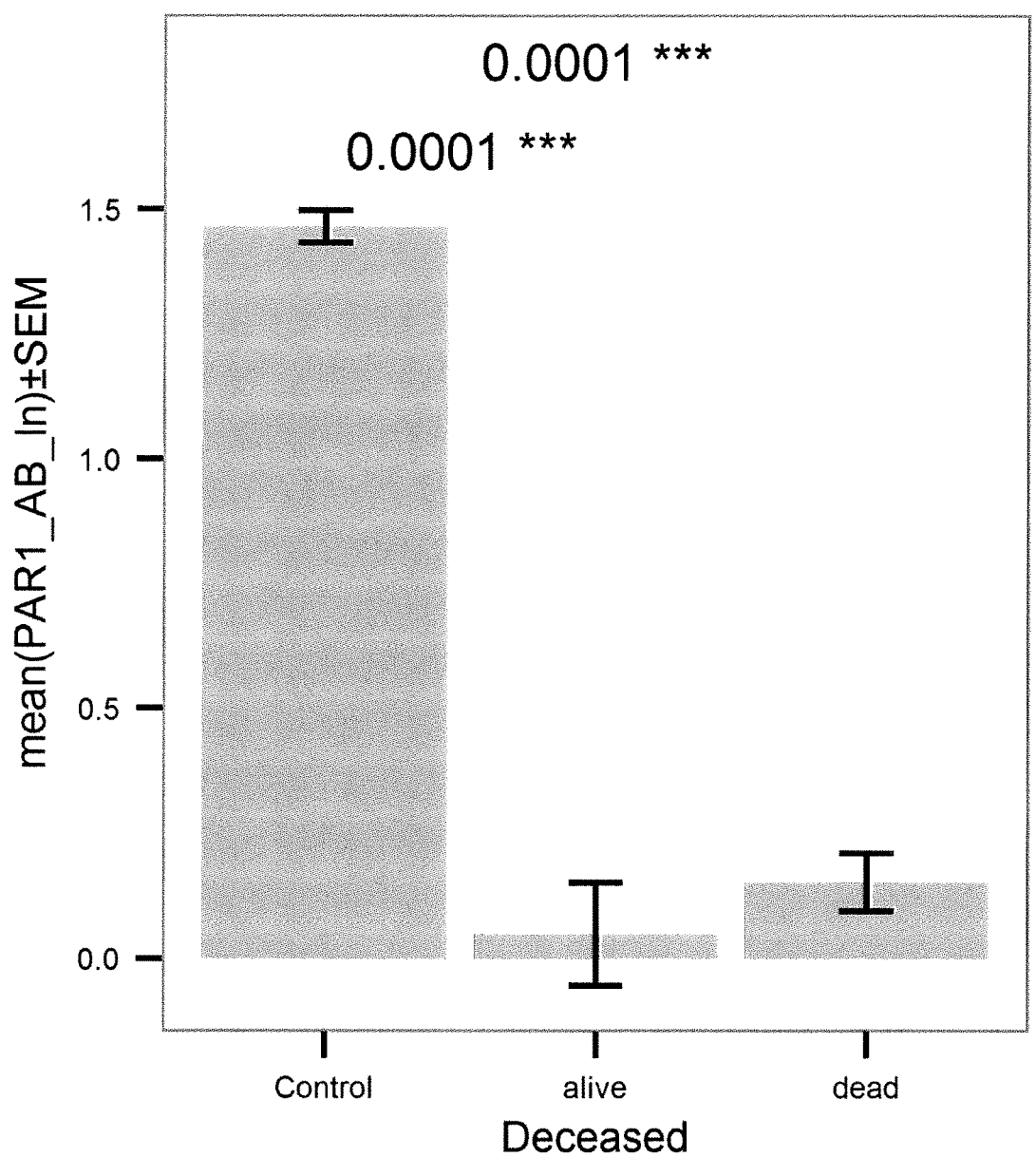

The sensitivity and specificity for levels of anti-PAR1 antibodies as predictor of relapse and/or mortality after treatment with a platinum analog was calculated using ROC-analysis and cutoff values were determined. The results for the prediction of relapse are given in FIG. 4A, for the prediction of mortality in FIG. 4B, and for the combined endpoint prediction (relapse or death) in FIG. 4C. FIG. 4D summarizes results for mortality of patients after chemotherapy. The results show that the levels of anti-PAR1 are a good predictor for relapse or mortality after treatment of cancer patients. The specificity and sensitivity of the prediction could be further enhanced when including further factors in a multivariate model.

These factors were age, Figo and histology staging.

Example 6

Figure 5:
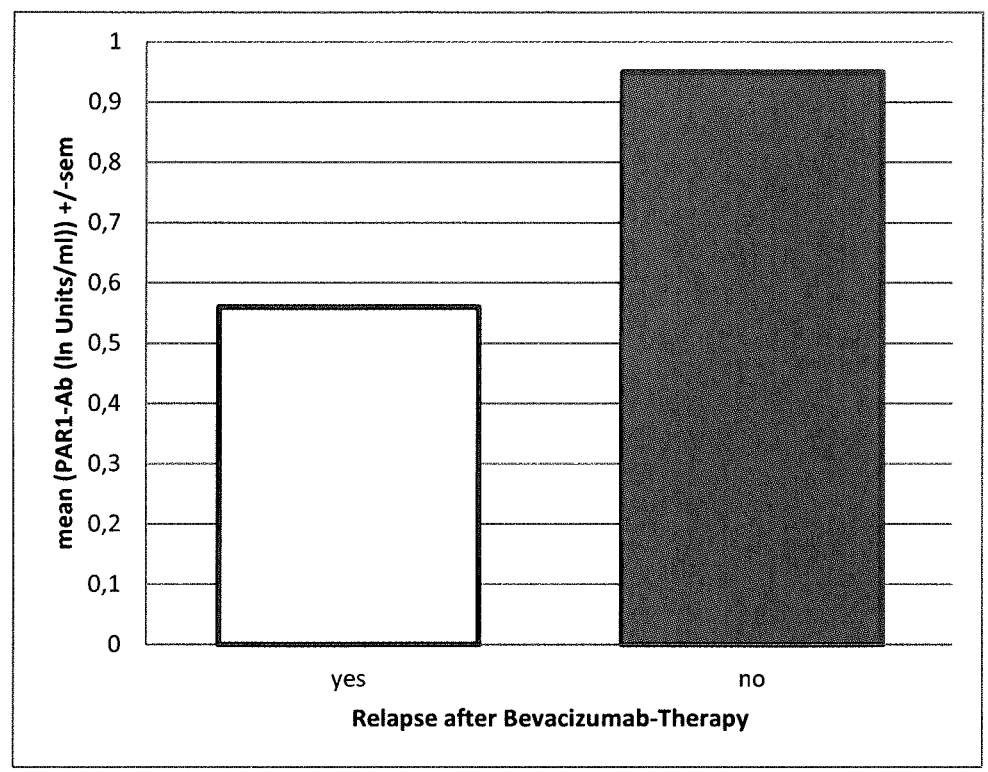
FIG. 5: Comparison of the mean level of anti-PAR1 antibodies (units/ml) in serum samples of ovarian cancer patients treated with bevacizumab. Relapse free after bevacizumab treatment show higher values (mean units/ml=0.95 units/ml, n=3) than patients with a relapse after becacizumab treatment (mean units/ml=0.56 units/ml, n=12). Bars indicate standard error of mean.

Serum samples of ovarian cancer patients were taken before treatment with Bevacizumab. The treatment was conducted by physicians. The patients were categorized into patients showing relapse, patients not showing relapse. Results are shown in FIG. 5. PAR1-antibody levels were lower in patients with relapse compared with the patients who had no relapse.

Example 7

Figure 6:
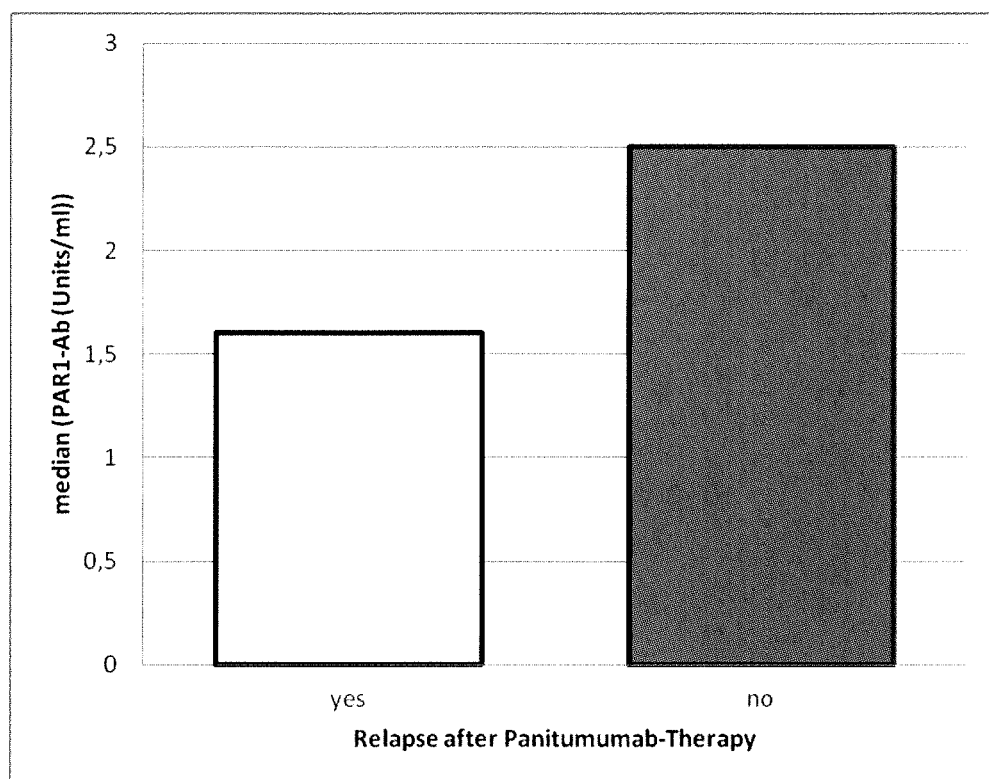
FIG. 6: Comparison of the mean level of anti-PAR1 antibodies (units/ml) in serum samples of ovarian cancer patients treated with panitumumab. Relapse free after panitumumab treatment show higher values (2.50 units/ml, n=3) than patients with a relapse after panitumumab treatment (1.60 units/ml, n=3).

Panitumumab is a humanized monoclonal antibody that is an EGFR inhibitor, inhibiting epidermal growth factor receptor activity (EGFR). Levels of autoantibodies directed against PAR1 in patients suffering from ovarian cancer were determined as outlined in Example 1 before panitumumab treatment. The patients were categorized into "yes" and "no", indicating whether they suffered from cancer relapse ("yes") after the treatment or not ("no"). Results are given in FIG. 6. Patients of the "no" group showed higher levels of anti PAR1 antibodies in samples as compared to patients of the "yes" group. This clearly shows that levels of anti PAR1 antibodies are a good predictor for the response to after treatment of cancer with an EGFR inhibitor.

Example 8

Figure 7:
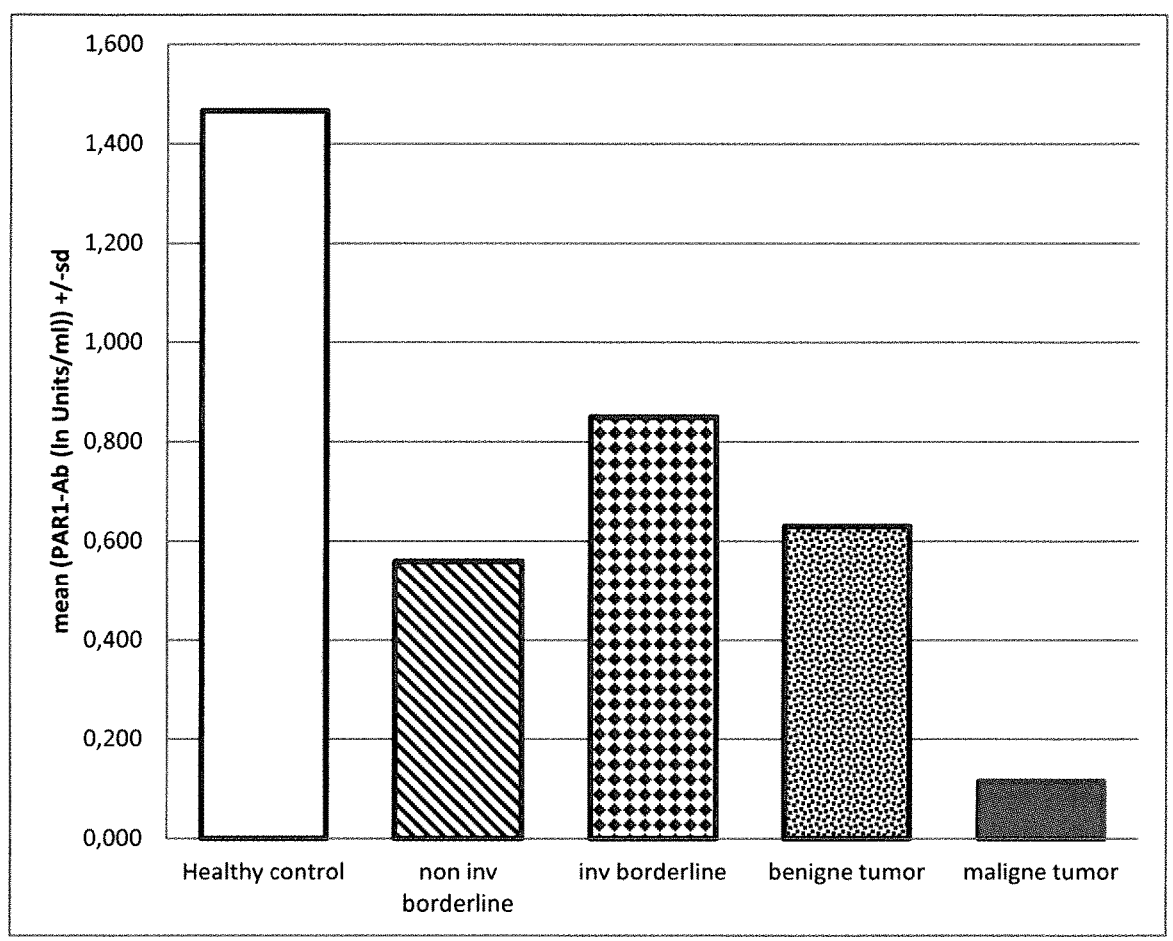
FIG. 7: Comparison of the mean level of anti-PAR1 antibodies (ln of units/ml) in serum samples of ovarian cancer patients suffering from malign (primary) ovarian Cancer ("malign"; mean=0.115; n=201) to the mean level of anti-PAR1 antibodies in serum samples of a ovarian cancer patients suffering from benign ovarian cancer ("benign", mean=0.63 units/ml, n=50) and healthy control subjects ("Control", mean=1.44 units/ml; n=132). Samples of patients having boarderline tumors (invasive or non-invasive) had levels comparable to those suffering from benign ovarian cancer. The p-value is indicated below. The p-values for all possible comparisons are significant.

Anti-PAR1 antibody levels in serum samples from 132 healthy donors ("control"; see Example 1), 201 patients with malign ovarian cancer and 50 patients with benign ovarian cancer, 38 patients with non-invasive borderline tumor patients and 12 patients with invasive borderline tumor patients were measured using the kit and method of example 1. The levels were determined in units/mL. FIG. 7 shows the mean values of the natural logarithm of the PAR1 antibody level for case and control subjects. Patient suffering from malign ovarian cancer of had significantly lower levels (p=0.001) of anti-PAR1 antibodies as compared to patients suffering from benign ovarian cancer, non-invasive or invasive borderline tumors or healthy controls, respectively. Benign ovarian cancer, non invasive or invasive borderline tumors had significantly lower levels (p=0.001) of anti-PAR1 antibodies as compared to healthy controls.

Example 9

Anti-PAR1 antibody levels in plasma samples of a healthy control group, patients suffering from metastatic cancer, patients suffering from solid organ cancer and patients suffering from squamous cell cancer of the skin were measured using the kit and method of Example 1, with the exception that plasma samples were used in a dilution of 1:100 for measurement of samples. The standard, however, was the same as in Example 1. The levels were determined in units/mL. FIG. 9 shows the mean values of the PAR1 antibody level. Patient suffering from the tested types of cancers had significantly lower levels of anti-PAR1 antibodies as compared to healthy controls.

Anti-PAR1 antibody levels were different between when merging all groups of patients suffering from cancer compared to the healthy control group (p=0.001).

Anti-PAR1 antibody levels were significantly different in plasma samples of metastatic cancer patients as compared to the healthy control (p=0.048); in plasma samples from patients suffering from a squamous cell carcinoma of the skin as compared to the healthy control (p=0.002); and in plasma of patients suffering from a solid organ cancer as compared to the healthy control (p=0.024).

Furthermore, ROC analysis for solid organ cancer and squamous cell carcinoma of the skin were performed and showed significant results (AUC 0.72 p=0.001).

Summary

The results of the present Examples show that anti-PAR1 antibody levels are significant lower in patients with the tested cancers, i.e. ovarian cancer, metastatic cancer, different solid organ cancers and squamous cell cancer of the skin, compared to healthy controls.

Furthermore, the levels are significantly higher in patients in which show no relapse after treatment with Bevacizumab. Also in patients in which no relapse occurs after treatment with panitumumab, significantly higher levels of anti-PAR1 antibodies can be detected.

Levels of anti-PAR1 antibody in patients suffering from an ovarian cancer with lower histological grades are higher compared to samples from patients suffering from ovarian cancer with lower grades. Levels of PAR1 antibodies in samples of patients are indicative for the degree of disease, i.e. the lower the level of antibodies, the higher the grade/degree of cancer. Furthermore, prediction of malign of benign tumors is possible.

Levels of anti-PAR1 antibodies in samples are a well suited predictor for the response to the treatment with an angiogenesis inhibitor or an inhibitor of EGFR activity. Relapse of cancer or mortality of the patient as endpoints of the treatment can be predicted.

The invention claimed is:

1. A method for treating cancer, comprising:
   (i) determining the level of antibodies against protease-activated receptor 1 (PAR1) in a sample from a mammal,
   (ii) comparing the determined level in the sample to a control level derived from control subjects without cancer;
   (iii) diagnosing the mammal with cancer if the level in the sample from the mammal as compared to the control level is decreased; and
   (iv) administering, to said mammal, a drug that is an angiogenesis inhibitor wherein said angiogenesis inhibitor is selected from the group consisting of bevacizumab and aflibercept, or an inhibitor of EGFR activity, wherein the inhibitor of EGFR activity is selected from the group consisting of panitumumab, trastuzumab, cetuximab, gefitinib, erlotinib, lapatinib, and vandetanib.

2. The method for treating cancer according to claim 1, wherein the mammal is diagnosed with cancer if the level of antibodies against PAR1 is less than 0.9 fold as compared to the control level from the control subjects without cancer.

3. A method for treating cancer, comprising:
   (i) determining the level of antibodies against protease-activated receptor 1 (PAR1) in a sample from a mammal;
   (ii) diagnosing the mammal as having cancer if the level of anti-PAR1 antibodies is below 2.7 units/ml; and
   (ii) administering, to said mammal, a drug that is an angiogenesis inhibitor, wherein said angiogenesis inhibitor is selected from the group consisting of bevacizumab and aflibercept, or an inhibitor of EGFR activity, wherein the inhibitor of EGFR activity is selected from the group consisting of panitumumab, trastuzumab, cetuximab, gefitinib, erlotinib, lapatinib, and vandetanib.

4. A method for treating cancer comprising:
   (i) determining the level of antibodies against protease-activated receptor 1 (PAR1) in a sample from a mammal,
   (ii) comparing the determined level in the sample to either one or both of a first and second PAR1 antibody control level,
      a) wherein the first PAR1 antibody control level is derived from first control subjects suffering from primary benign tumor, and
      b) wherein the second PAR1 antibody control level is derived from second control subjects suffering from primary malignant cancer,
   (iii.a) diagnosing the mammal with primary malignant cancer if the level in the sample from the mammal is decreased, as compared to the first PAR1 antibody control level; and/or is equal, as compared to the second PAR1 antibody control level; and
   (iii.b) diagnosing the mammal with a benign tumor if the level in the sample from the mammal is increased, as compared to the second PAR1 antibody control level; and/or is equal, as compared to the first PAR1 antibody control level is; and
   (iv) administering, to said mammal, a drug that is an angiogenesis inhibitor, wherein said angiogenesis inhibitor is selected from the group consisting of bevacizumab and aflibercept, or an inhibitor of EGFR activity, wherein the inhibitor of EGFR activity is selected from the group consisting of panitumumab, trastuzumab, cetuximab, gefitinib, erlotinib, lapatinib, and vandetanib.

5. The method for treating cancer according to claim 4, wherein the mammal is diagnosed as having a malignant cancer if the level of antibodies against PAR1 in the sample from the mammal is less than 0.9 fold as compared to the first PAR1 antibody control level, and wherein the mammal is diagnosed as having a benign tumor if the level of antibodies against PAR1 in the sample from the mammal is more than 1.1 fold as compared to the second PAR1 antibody control level.

6. A method for treating cancer comprising:
   (i) determining the level of antibodies against PAR1 in a sample from a mammal,
   (ii) comparing the determined level in the sample to either one or both of a first and second PAR1 antibody control level,
      a) wherein the first PAR1 antibody control level is derived from first control subjects suffering from a cancer classified as Grade II or Grade III cancer, optionally Grade II or Grade III solid organ cancer, and
      b) wherein the second PAR1 antibody control level is derived from a second control subject suffering from a cancer classified as Grade I cancer, optionally Grade I solid organ cancer,
   (iii.a) diagnosing the mammal as having Grade I cancer if the level in the sample from the mammal is increased, as compared to the first PAR1 antibody control level; and/or is equal, as compared to the second PAR1 antibody control level; and
   (iii.b) diagnosing the mammal as having Grade II or Grade III cancer if the level in the sample from the mammal is decreased, as compared to the second PAR1 antibody control level; and/or is equal, as compared to the first PAR1 antibody control level; and
(iv) administering, to said mammal, a drug that is an angiogenesis inhibitor, wherein said angiogenesis inhibitor is selected from the group consisting of bevacizumab and aflibercept, or an inhibitor of EGFR activity, wherein the inhibitor of EGFR activity is selected from the group consisting of panitumumab, trastuzumab, cetuximab, gefitinib, erlotinib, lapatinib, and vandetanib.

7. The method for treating cancer according to claim 6, wherein the mammal is diagnosed as having Grade II or Grade III cancer if the level of antibodies against PAR1 in the sample from the subject of mammal is less than 0.9 fold as compared to the second PAR1 antibody control level, and wherein the mammal is diagnosed as having Grade I cancer if the level of antibodies against PAR1 in the sample from the mammal is more than 1.1 fold as compared to the first PAR1 antibody control level.

8. The method according to claim 1, wherein the cancer is selected from the group consisting of ovarian cancer, a solid organ cancer, squamous cell carcinoma, squamous cell carcinoma, metastatic cancer, breast cancer, lung cancer, colorectal cancer, colon cancer, renal cancer, pancreatic cancer, prostate cancer, gastric cancer, liver cancer, and a glioblastoma.

9. A method for treating ovarian cancer in a mammal comprising:
(i) determining the level of antibodies against protease-activated receptor 1 (PAR1) in a sample from the mammal, and
(ii) comparing the determined level in the sample to either one or both of a first and second PAR1 antibody control level,
   a) wherein the first PAR1 antibody control level is derived from first control subjects suffering from high grade serous ovarian cancer (HGSOC), and
   b) wherein the second PAR1 antibody control level is derived from second control subjects suffering from low grade serous ovarian cancer (LGSOC),
(iii.a) diagnosing the mammal as having LGSOC if the level in the sample from the mammal is increased, as compared to the first PAR1 antibody control level and/or is equal, as compared to the second PAR1 antibody control level; and
(iii.b) diagnosing the mammal as having HGSOC if the level in the sample from the mammal is decreased, as compared to the second PAR1 antibody control level and/or is equal, as compared to the first PAR1 antibody control level; and
(iv) administering, to said mammal, a drug that is an angiogenesis inhibitor, wherein said angiogenesis inhibitor is selected from the group consisting of bevacizumab and aflibercept, or an inhibitor of EGFR activity, wherein the inhibitor of EGFR activity is selected from the group consisting of panitumumab, trastuzumab, cetuximab, gefitinib, erlotinib, lapatinib, and vandetanib.

10. The method for treating cancer according to claim 9, wherein a mammal is diagnosed as having HGSOC if the level of antibodies against PAR1 in the sample from the mammal is less than 0.9 fold as compared to the second PAR1 antibody control; and wherein a mammal is diagnosed as having LGSOC if the level of antibodies against PAR1 in the sample from the mammal is more than 1.1 fold as compared to the first PAR1 antibody control level.

11. A method for the treatment of cancer comprising:
(i) determining the level of antibodies against protease-activated receptor 1 (PAR1) in a sample from a mammal; and
(ii) comparing the determined level in the sample to either one or both of a first and a second PAR1 antibody control level,
   a) wherein the first PAR1 antibody control level is derived from first control subjects responding to said treatment, and
   b) wherein the second PAR1 antibody control level is derived from second control subjects not responding to said treatment,
(iii.a) determining the mammal to be non-responsive to the treatment if the level in the sample from the mammal is decreased, as compared to the first PAR1 antibody control level and/or is equal, as compared to the second PAR1 antibody control level, and
(iii.b) determining the mammal to be responsive to the treatment if the level in the sample from the mammal is increased, as compared to the second PAR1 antibody control level and/or is equal, as compared to the first PAR1 antibody control level; and
(iv) administering, to the mammal determined to be responsive to the treatment, a drug that is an angiogenesis inhibitor, wherein said angiogenesis inhibitor is selected from the group consisting of bevacizumab and aflibercept, or a drug that is an inhibitor of EGFR activity, wherein the inhibitor of EGFR activity is selected from the group consisting of panitumumab, trastuzumab, cetuximab, gefitinib, erlotinib, lapatinib, and vandetanib.

12. The method according to claim 11, wherein a mammal is determined to be non-responsive to said treatment if the level of antibodies against PAR1 in the sample from the mammal is less than 0.9 fold as compared to the first PAR1 antibody control level, and wherein a mammal is determined to be responsive to said treatment if the level of antibodies against PAR1 in the sample from the mammal is more than 1.1 fold as compared to the second PAR1 antibody control level.

13. The method according to claim 11, wherein the cancer is selected from the group consisting of ovarian cancer, a solid organ cancer, squamous cell carcinoma, squamous cell carcinoma, metastatic cancer, breast cancer, lung cancer, colorectal cancer, colon cancer, renal cancer, pancreatic cancer, prostate cancer, gastric cancer, liver cancer, and a glioblastoma.

14. The method according to claim 1, wherein the anti-PAR1 antibody is detected in an immunoassay.

15. The method according to claim 14, wherein the immunoassay is selected from the group of immunoprecipitation, enzyme immunoassay (EIA), radioimmunoassay (RIA), enzyme-linked immunosorbent assay (ELISA), fluorescent immunoassay, a chemiluminescent assay, an agglutination assay, nephelometric assay, turbidimetric assay, a Western Blot, a competitive immunoassay, a noncompetitive immunoassay, a homogeneous immunoassay a heterogeneous immunoassay, a bioassay, a reporter assay, a luciferase assay, and a FACS based immunoassay.

16. The method according to claim 1, wherein the sample is plasma or serum.

17. The method according to claim 1, comprising
(a) contacting the sample with protease-activated receptor 1 (PAR1) or an antigenic peptide fragment thereof under conditions allowing for formation of a complex between anti-PAR1 antibodies with PAR1 or a peptide fragment thereof, and (b) detecting the complex.

18. The method according to claim 17, wherein the PAR1 or the peptide fragment thereof is immobilized on a surface.

19. The method according to claim 17, wherein the complex is detected using a secondary antibody against the Fc portion of the anti-PAR1 antibody.

20. The method according to claim 19, wherein the anti-PAR1 antibody is an IgG-antibody and the secondary antibody is an anti-IgG antibody.

21. The method according to claim 19, wherein the secondary antibody is labeled with a detectable marker.

22. The method according to claim 1, wherein the presence of one or more further markers for cancer is detected in the sample.

23. The method according to claim 11, comprising administering the angiogenesis inhibitor when the level of anti-PAR1 antibodies in a sample from the mammal determined to be responsive to the treatment is above 0.6 units/ml.

24. The method according to claim 11, comprising administering the angiogenesis inhibitor when the level of anti-PAR1 antibodies in a sample from the mammal determined to be responsive to the treatment is above 1.5 units/ml.

25. The method according to claim 11, wherein the cancer is ovarian cancer.

* * * * *

SEQUENCE LISTING

<160> NUMBER OF SEQ ID NOS: 2

<210> SEQ ID NO 1
<211> LENGTH: 425
<212> TYPE: PRT
<213> ORGANISM: Homo sapiens
<220> FEATURE:
<221> NAME/KEY: MISC_FEATURE
<222> LOCATION: (1)..(425)
<223> OTHER INFORMATION: Amino acid sequence of the human PAR1 receptor
       (isoform 1)

<400> SEQUENCE: 1

```
Met Gly Pro Arg Arg Leu Leu Leu Val Ala Ala Cys Phe Ser Leu Cys
1               5                   10                  15
Gly Pro Leu Leu Ser Ala Arg Thr Arg Ala Arg Arg Pro Glu Ser Lys
            20                  25                  30
Ala Thr Asn Ala Thr Leu Asp Pro Arg Ser Phe Leu Leu Arg Asn Pro
        35                  40                  45
Asn Asp Lys Tyr Glu Pro Phe Trp Glu Asp Glu Lys Asn Glu Ser
    50                  55                  60
Gly Leu Thr Glu Tyr Arg Leu Val Ser Ile Asn Lys Ser Ser Pro Leu
65                  70                  75                  80
Gln Lys Gln Leu Pro Ala Phe Ile Ser Glu Asp Ala Ser Gly Tyr Leu
                85                  90                  95
Thr Ser Ser Trp Leu Thr Leu Phe Val Pro Ser Val Tyr Thr Gly Val
            100                 105                 110
Phe Val Val Ser Leu Pro Leu Asn Ile Met Ala Ile Val Val Phe Ile
        115                 120                 125
Leu Lys Met Lys Val Lys Pro Ala Val Val Tyr Met Leu His Leu
    130                 135                 140
Ala Thr Ala Asp Val Leu Phe Val Ser Val Leu Pro Phe Lys Ile Ser
145                 150                 155                 160
Tyr Tyr Phe Ser Gly Ser Asp Trp Gln Phe Gly Ser Glu Leu Cys Arg
                165                 170                 175
Phe Val Thr Ala Ala Phe Tyr Cys Asn Met Tyr Ala Ser Ile Leu Leu
            180                 185                 190
Met Thr Val Ile Ser Ile Asp Arg Phe Leu Ala Val Val Tyr Pro Met
            195                 200                 205
Gln Ser Leu Ser Trp Arg Thr Leu Gly Arg Ala Ser Phe Thr Cys Leu
    210                 215                 220
Ala Ile Trp Ala Leu Ala Ile Ala Gly Val Val Pro Leu Leu Leu Lys
225                 230                 235                 240
Glu Gln Thr Ile Gln Val Pro Gly Leu Asn Ile Thr Thr Cys His Asp
                245                 250                 255
Val Leu Asn Glu Thr Leu Leu Glu Gly Tyr Tyr Ala Tyr Tyr Phe Ser
            260                 265                 270
Ala Phe Ser Ala Val Phe Phe Val Pro Leu Ile Ile Ser Thr Val
    275                 280                 285
Cys Tyr Val Ser Ile Ile Arg Cys Leu Ser Ser Ser Ala Val Ala Asn
    290                 295                 300
Arg Ser Lys Lys Ser Arg Ala Leu Phe Leu Ser Ala Ala Val Phe Cys
305                 310                 315                 320
Ile Phe Ile Ile Cys Phe Gly Pro Thr Asn Val Leu Leu Ile Val His
            325                 330                 335
Tyr Ser Phe Leu Ser His Thr Ser Thr Glu Ala Ala Tyr Phe Ala
            340                 345                 350
Tyr Leu Leu Cys Val Cys Val Ser Ser Ile Ser Cys Cys Ile Asp Pro
        355                 360                 365
Leu Ile Tyr Tyr Tyr Ala Ser Ser Glu Cys Gln Arg Tyr Val Tyr Ser
    370                 375                 380
Ile Leu Cys Cys Lys Glu Ser Ser Asp Pro Ser Ser Tyr Asn Ser Ser
385                 390                 395                 400
Gly Gln Leu Met Ala Ser Lys Met Asp Thr Cys Ser Ser Asn Leu Asn
                405                 410                 415
Asn Ser Ile Tyr Lys Lys Leu Leu Thr
```

```
                    420                 425

<210> SEQ ID NO 2
<211> LENGTH: 425
<212> TYPE: PRT
<213> ORGANISM: Homo sapiens
<220> FEATURE:
<221> NAME/KEY: MISC_FEATURE
<222> LOCATION: (1)..(425)
<223> OTHER INFORMATION: Amino acid sequence of the human PAR1 receptor
      (isoform 2)

<400> SEQUENCE: 2

Met Gly Pro Arg Arg Leu Leu Leu Val Ala Ala Cys Phe Ser Leu Cys
1               5                   10                  15

Gly Pro Leu Leu Ser Ala Arg Thr Arg Ala Arg Arg Pro Glu Ser Lys
            20                  25                  30

Ala Thr Asn Ala Thr Leu Asp Pro Arg Ser Phe Leu Leu Arg Asn Pro
        35                  40                  45

Asn Asp Lys Tyr Glu Pro Phe Trp Glu Asp Glu Glu Lys Asn Glu Ser
    50                  55                  60

Gly Leu Thr Glu Tyr Arg Leu Val Ser Ile Asn Lys Ser Ser Pro Leu
65                  70                  75                  80

Gln Lys Gln Leu Pro Ala Phe Ile Ser Glu Asp Ala Ser Gly Tyr Leu
                85                  90                  95

Thr Ser Ser Trp Leu Thr Leu Phe Val Pro Ser Val Tyr Thr Gly Val
            100                 105                 110

Phe Val Val Ser Leu Pro Leu Asn Ile Met Ala Ile Val Val Phe Ile
        115                 120                 125

Leu Lys Met Lys Val Lys Lys Pro Ala Val Val Tyr Met Leu His Leu
130                 135                 140

Ala Thr Ala Asp Val Leu Phe Val Ser Val Leu Pro Phe Lys Ile Ser
145                 150                 155                 160

Tyr Tyr Phe Ser Gly Ser Asp Trp Gln Phe Gly Ser Glu Leu Cys Arg
                165                 170                 175

Phe Val Thr Ala Ala Phe Tyr Cys Asn Met Tyr Ala Ser Ile Leu Leu
            180                 185                 190

Met Thr Val Ile Ser Ile Asp Arg Phe Leu Ala Val Val Tyr Pro Met
        195                 200                 205

Gln Ser Leu Ser Trp Arg Thr Leu Gly Arg Ala Ser Phe Thr Cys Leu
    210                 215                 220

Ala Ile Trp Ala Leu Ala Ile Ala Gly Val Val Pro Leu Leu Leu Lys
225                 230                 235                 240

Glu Gln Thr Ile Gln Val Pro Gly Leu Asn Ile Thr Thr Cys His Asp
                245                 250                 255

Val Leu Asn Glu Thr Leu Leu Glu Gly Tyr Tyr Ala Tyr Tyr Phe Ser
            260                 265                 270

Ala Phe Ser Ala Val Phe Phe Val Pro Leu Ile Ile Ser Thr Val
        275                 280                 285

Cys Tyr Val Ser Ile Ile Arg Cys Leu Ser Ser Ser Ala Val Ala Asn
    290                 295                 300

Arg Ser Lys Lys Ser Arg Ala Leu Phe Leu Ser Ala Ala Val Phe Cys
305                 310                 315                 320

Ile Phe Ile Ile Cys Phe Gly Pro Thr Asn Val Leu Leu Ile Ala His
                325                 330                 335

Tyr Ser Phe Leu Ser His Thr Ser Thr Thr Glu Ala Ala Tyr Phe Ala
```

-continued

```
                    340                 345                 350
Tyr Leu Leu Cys Val Cys Val Ser Ser Ile Ser Cys Cys Ile Asp Pro
                355                 360                 365

Leu Ile Tyr Tyr Tyr Ala Ser Ser Glu Cys Gln Arg Tyr Val Tyr Ser
        370                 375                 380

Ile Leu Cys Cys Lys Glu Ser Ser Asp Pro Ser Ser Tyr Asn Ser Ser
385                 390                 395                 400

Gly Gln Leu Met Ala Ser Lys Met Asp Thr Cys Ser Ser Asn Leu Asn
                405                 410                 415

Asn Ser Ile Tyr Lys Lys Leu Leu Thr
            420                 425
```